US011352606B2

(12) United States Patent
Gerecht et al.

(10) Patent No.: US 11,352,606 B2
(45) Date of Patent: Jun. 7, 2022

(54) LOW OXYGEN TENSION ENHANCES ENDOTHELIAL FATE OF HUMAN PLURIPOTENT STEM CELLS

(71) Applicant: THE JOHNS HOPKINS UNIVERSITY, Baltimore, MD (US)

(72) Inventors: Sharon Gerecht, Baltimore, MD (US); Sravanti Kusuma, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 78 days.

(21) Appl. No.: 15/115,718

(22) PCT Filed: Mar. 17, 2014

(86) PCT No.: PCT/US2014/030616
§ 371 (c)(1),
(2) Date: Aug. 1, 2016

(87) PCT Pub. No.: WO2015/119642
PCT Pub. Date: Aug. 13, 2015

(65) Prior Publication Data
US 2017/0009204 A1  Jan. 12, 2017

Related U.S. Application Data

(60) Provisional application No. 61/938,062, filed on Feb. 10, 2014.

(51) Int. Cl.
*C12N 5/071* (2010.01)
*A61K 35/44* (2015.01)
*A61K 35/545* (2015.01)

(52) U.S. Cl.
CPC .............. *C12N 5/069* (2013.01); *A61K 35/44* (2013.01); *A61K 35/545* (2013.01); *C12N 2500/02* (2013.01); *C12N 2501/15* (2013.01); *C12N 2501/165* (2013.01); *C12N 2506/02* (2013.01); *C12N 2506/45* (2013.01); *C12N 2533/54* (2013.01)

(58) Field of Classification Search
None
See application file for complete search history.

(56) References Cited

U.S. PATENT DOCUMENTS

| 5,453,357 | A | 9/1995 | Hogan |
| 5,670,372 | A | 9/1997 | Hogan |
| 5,690,926 | A | 11/1997 | Hogan |
| 5,833,948 | A | 11/1998 | Tournier et al. |
| 5,843,780 | A | 12/1998 | Thomson |
| 6,200,806 | B1 | 3/2001 | Thomson |
| 6,251,671 | B1 | 6/2001 | Hogan et al. |
| 8,268,621 | B2 | 9/2012 | Turovets et al. |
| 2002/0038152 | A1 | 3/2002 | Naughton |
| 2008/0299091 | A1 | 12/2008 | Revazova et al. |
| 2010/0216181 | A1* | 8/2010 | Daigh ................... C12N 5/0606 435/29 |
| 2010/0279403 | A1* | 11/2010 | Rajesh ................. C12N 5/0647 435/366 |
| 2011/0305672 | A1* | 12/2011 | Dalton ................. C12N 5/0606 424/93.7 |
| 2012/0148546 | A1 | 6/2012 | Kar-Oaknin et al. |
| 2012/0295347 | A1* | 11/2012 | Kessler ................ C12N 5/0692 435/366 |

FOREIGN PATENT DOCUMENTS

WO  2011/073521 A1  6/2011

OTHER PUBLICATIONS

Miettinen et al. "Glomus tumor cells: evaluation of smooth muscle and endothelial cell properties." Virchows Archiv B 43.1 (1983): 139-149. (Year: 1983).*
STEMCELL Technologies "Human Recombinant VEGF-165", available from company's website <https://www.stemcell.com/human-recombinant-vegf-165.html>, copright 2021, accessed Aug. 12, 2021. (Year: 2021).*
Xu et al. "Efficient commitment to functional CD34+ progenitor cells from human bone marrow mesenchymal stem-cell-derived induced pluripotent stem cells." PLoS One 7.4 (2012): e34321. (Year: 2012).*
Kohler et al. "Flk1+ and VE-cadherin+ endothelial cells derived from iPSCs recapitulates vascular development during differentiation and display similar angiogenic potential as ESC-derived cells." PloS one 8.12 (2013): e85549. (Year: 2013).*

(Continued)

*Primary Examiner* — Emily A Cordas
(74) *Attorney, Agent, or Firm* — DLA Piper LLP (US)

(57) ABSTRACT

Low oxygen tension is a critical regulator of the developing or regenerating vasculature. The present invention is based on the determination that low oxygen tension during early stages of early vascular cell (EVC) derivation induces endothelial commitment and maturation of pluripotent stem cells. Inhibition of reactive oxygen species generation during the early stages of differentiation abrogates the endothelial inductive effects of the low oxygen environments. Methods of generating various types of cells from pluripotent stem cells (PSCs) are described, as well as compositions and methods of use thereof. In particular, generation of EVCs, bicellular vascular populations, early endothelial cells (ECs) and pericytes via culture in a low oxygen environment is described.

14 Claims, 9 Drawing Sheets

(56) References Cited

OTHER PUBLICATIONS

Orlova et al. "Functionality of endothelial cells and pericytes from human pluripotent stem cells demonstrated in cultured vascular plexus and zebrafish xenografts." Arteriosclerosis, Thrombosis, and Vascular Biology 34.1 (originally published Oct. 24, 2013): 177-186. (Year: 2013).*
James, et al., Expansion and maintenance of human embryonic stem cell-derived endothelial cells by TGFbeta inhibition is Id1 dependent. Nat Biotechnol. Feb. 2010;28(2):161-6.
Cheng, et al., Low incidence of DNA sequence variation in human induced pluripotent stem cells generated by non-integrating plasmid expression. Cell Stem Cell. Mar. 2, 2012; 10(3): 337-344.
Chou, et al., Efficient human iPS cell derivation by a non-integrating plasmid from blood cells with unique epigenetic and gene expression signatures. Cell Res. Mar. 2011;21(3):518-29.
Vo, et al., Smooth-muscle-like cells derived from human embryonic stem cells support and augment cord-like structures in vitro. Stem Cell Rev. Jun. 2010;6(2):237-47.
Wanjare, et al., Derivation and maturation of synthetic and contractile vascular smooth muscle cells from human pluripotent stem cells. Cardiovasc Res. Feb. 1, 2013;97(2):321-30.
Kusuma, et al., The extracellular matrix is a novel attribute of endothelial progenitors and of hypoxic mature endothelial cells. FASEB J. Dec. 2012;26(12):4925-4936.
Abaci, et al., Adaptation to oxygen deprivation in cultures of human pluripotent stem cells, endothelial progenitor cells, and umbilical vein endothelial cells. Am J Physiol Cell Physiol. Jun. 2010;298(6):C1527-C1537.
Abaci, et al., Design and development of microbioreactors for long-term cell culture in controlled oxygen microenvironments. Biomed Microdevices. 2012;14:145-152.
Abaci, et al., Unforeseen decreases in dissolved oxygen levels affect tube formation kinetics in collagen gels. Am J Physiol Cell Physiol. Aug. 2011;301(2):C431-C440.
Abaci, et al., Microbioreactors to manipulate oxygen tension and shear stress in the microenvironment of vascular stem and progenitor cells. Biotechnol Appl Biochem. Mar.-Apr. 2012;59(2):97-105.
Kusuma, et al., Self-organized vascular networks from human pluripotent stem cells in a synthetic matrix. Proc Natl Acad Sci USA. Jul. 2013;110(31):12601-12606.
Paternotte, et al., Review: behaviour of endothelial cells faced with hypoxia. Biomed Mater Eng. 2008;18(4-5):295-9.
Ma, et al., Hypoxia and stem cell-based engineering of mesenchymal tissues. Biotechnol Prog. Jan.-Feb. 2009;25(1):32-42.
Kumar, et al., An Oxygen Transport Model for Human Bone Marrow Microcirculation. Food Bioprod Process. Jun. 2004;82(2):105-116.
Prado-Lopez, et al., Hypoxia Promotes Efficient Differentiation of Human Embryonic Stem Cells to Functional Endothelium. Stem Cells. 2010;28:407-418.
Thannickal, et al., Reactive oxygen species in cell signaling. Am J Physiol Lung Cell Mol Physiol. Dec. 2000;279(6):L1005-28.
LifeMapEmbryonic (2012).
Filopodia (2012), definition.
Pittenger, et al., Multilineage potential of adult human mesenchymal stem cells. Science. Apr. 2, 1999;284(5411):143-7.
Grayson, et al., Engineering anatomically shaped human bone grafts. Proc Natl Acad Sci U S A. Feb. 23, 2010;107(8):3299-304.
Khetan, et al., Sequential crosslinking to control cellular spreading in 3-dimensional hydrogels. Soft Matter. 2009;5(8):1601-1606.
Khetan, et al., Patterning network structure to spatially control cellular remodeling and stem cell fate within 3-dimensional hydrogels. Biomaterials. Nov. 2010;31(32):8228-34.
Kang, et al., Bioengineered human vascular networks transplanted into secondary mice reconnect with the host vasculature and re-establish perfusion. Blood. Dec. 15, 2011;118(25):6718-21.
Hanjaya-Putra, et al., Controlled activation of morphogenesis to generate a functional human microvasculature in a synthetic matrix. Blood. Jul. 21, 2011;118(3):804-15.
Mead, et al., Isolation and characterization of endothelial progenitor cells from human blood. Curr Protoc Stem Cell Biol. Jul. 2008;Chapter 2:Unit 2C.1.
Thomson, et al., Embryonic stem cell lines derived from human blastocysts. Science. Nov. 6, 1998;282(5391):1145-7.
Shin, et al., Enhancement of differentiation efficiency of hescs into vascular lineage cells in hypoxia via a paracrine mechanism. Stem Cell Research. 2011;7:173-185.
Lee, et al., Hypoxic priming of mescs accelerates vascular-lineage differentiation through hif1-mediated inverse regulation of oct4 and vegf. EMBO Molecular Medicine. 2012;4:924-938.
Akita, et al., Hypoxic preconditioning augments efficacy of human endothelial progenitor cells for therapeutic neovascularization. Laboratory Investigation. 2003;83:65-73.
Ong, et al., Hypoxic/normoxic preconditioning increases endothelial differentiation potential of human bone marrow cd133+ cells. Tissue Engineering—Part C: Methods. 2010;16:1069-1081.
Maruyama, et al., Hypoxia enhances the induction of human amniotic mesenchymal side population cells into vascular endothelial lineage. International Journal of Molecular Medicine. 2013;32:315-322.
Gassmann, et al., Oxygen supply and oxygen-dependent gene expression in differentiating embryonic stem cells. Proceedings of the National Academy of Sciences of the United States of America. 1996;93:2867-2872.
Ramirez-Bergeron, et al., Hypoxia affects mesoderm and enhances hemangioblast specification during early development. Development. 2004;131:4623-4634.
Sone, et al., Pathway for differentiation of human embryonic stem cells to vascular cell components and their potential for vascular regeneration. Arteriosclerosis Thrombosis and Vascular Biology. 2007;27:2127-2134.
Hill, et al., Human embryonic stem cell-derived vascular progenitor cells capable of endothelial and smooth muscle cell function. Experimental Hematology. 2010;38:246-257.e241.
Bai, et al., Bmp4 regulates vascular progenitor development in human embryonic stem cells through a smad-dependent pathway. Journal of Cellular Biochemistry. 2010;109:363-374.
Yang, et al., Human cardiovascular progenitor cells develop from a kdr+ embryonic-stem-cell-derived population. Nature. 2008;453:524-528.
Wang, et al., Endothelial cells derived from human embryonic stem cells form durable blood vessels in vivo. Nature Biotechnology. 2007;25:317-318.
Ferreira, et al., Vascular progenitor cells isolated from human embryonic stem cells give rise to endothelial and smooth muscle-like cells and form vascular networks in vivo. Circulation Research. 2007;101:286-294.
Park, et al., Efficient differentiation of human pluripotent stem cells into functional cd34+ progenitor cells by combined modulation of the mek/erk and bmp4 signaling pathways. Blood. 2010;116:5762-5772.
Evseenko, et al., Mapping the first stages of mesoderm commitment during differentiation of human embryonic stem cells. Proceedings of the National Academy of Sciences of the United States of America. 2010;107:13742-13747.
Chandel, et al., Mitochondrial reactive oxygen species trigger hypoxia-induced transcription. Proceedings of the National Academy of Sciences. 1998;95:11715-11720.
Schmelter, et al., Embryonic stem cells utilize reactive oxygen species as transducers of mechanical strain-induced cardiovascular differentiation. FASEB Journal. 2006;20:E294-E306.
Ji, et al., Reactive oxygen species enhance differentiation of human embryonic stem cells into mesendodermal lineage. Experimental and Molecular Medicine. 2010;42:175-186.
Claxton, et al., Oxygen modifies artery differentiation and network morphogenesis in the retinal vasculature. Developmental Dynamics. 2005;233:822-828.

(56) References Cited

OTHER PUBLICATIONS

Diez, et al., Hypoxia-mediated activation of dll4-notch-hey2 signaling in endothelial progenitor cells and adoption of arterial cell fate. Experimental Cell Research. 2007;313:1-9.

Obi, et al., Fluid shear stress induces arterial differentiation of endothelial progenitor cells. Journal of Applied Physiology. 2009;106:203-211.

Narazaki, et al., Directed and systematic differentiation of cardiovascular cells from mouse induced pluripotent stem cells. Circulation. 2008;118:498-506.

Pham, et al., Hypoxia upregulates vegf expression in alveolar epithelial cells in vitro and in vivo. American Journal of Physiology—Lung Cellular and Molecular Physiology. 2002;283:L1133-L1142.

Lawson, et al., Sonic hedgehog and vascular endothelial growth factor act upstream of the notch pathway during arterial endothelial differentiation. Developmental Cell. 2002;3:127-136.

Lanner, et al., Functional arterial and venous fate is determined by graded vegf signaling and notch status during ambryonic stem cell differentiation. Arteriosclerosis, Thrombosis, and Vascular Biology. 2007;27:487-493.

Lanner, et al., Hypoxia-induced arterial differentiation requires adrenomedullin and notch signaling. Stem Cells and Development. 2013;22:1360-1369.

Chuikov, et al., Prdm16 promotes stem cell maintenance in multiple tissues, partly by regulating oxidative stress. Nature Cell Biology. 2010;12:999-1006.

Liu, et al., Bmi1 regulates mitochondrial function and the DNA damage response pathway. Nature. 2009;459:387-392.

Mali, et al., Butyrate greatly enhances derivation of human induced pluripotent stem cells by promoting epigenetic remodeling and the expression of pluripotency-associated genes. Stem Cells. Apr. 2010;28(4):713-20.

Haase, et al., Generation of induced pluripotent stem cells from human cord blood. Cell Stem Cell. Oct. 2, 2009;5(4):434-41.

Dickinson, et al., Guiding endothelial progenitor cell tube formation using patterned fibronectin surfaces. Soft Matter. 2010;6(20):5109-5119.

Orlidge, et al., Inhibition of capillary endothelial cell growth by pericytes and smooth muscle cells. J Cell Biol. Sep. 1987;105(3):1455-62.

* cited by examiner

LOW OXYGEN TENSION ENHANCES ENDOTHELIAL FATE OF HUMAN PLURIPOTENT STEM CELLS

CROSS-REFERENCE TO RELATED APPLICATIONS

This application is a 35 U.S.C. § 371 U.S. national entry of International Application PCT/US2014/030616, having an international filing date of Mar. 17, 2014, which claims the benefit of U.S. Provisional Application No. 61/938,062, filed Feb. 10, 2014, the content of each of the aforementioned applications is herein incorporated by reference in their entirety.

STATEMENT OF GOVERNMENT INTEREST

This invention was made with government support under grant number HL112644, HL107938, CA143868, awarded by the National Institutes of Health, and grant number 1054415, awarded by the National Science Foundation. The Government has certain rights in the invention.

BACKGROUND

Field of Invention

The present invention relates generally to pluripotent stem cells (PSCs) and more specifically to differentiation of PSCs under hypoxic conditions toward early vascular cells (EVCs).

Background Information

Low oxygen environments drive blood vessel growth in both the embryo and the adult. In the developing human embryo, the earliest tissue to form is the vascular system due to the necessity of oxygen and nutrients for tissue growth and survival. In the adult, ischemia, characterized by a deficit in nutrients and oxygen, stimulates blood vessel recruitment. In stark contrast to typical cell culture environments that consist of approximately 20% $O_2$, tissues in the body experience 1-5% $O_2$ and blood vessels experience 5-7% $O_2$ based on vessel type.

Human stem cells provide the opportunity to study the effects of low oxygen environments on vascular differentiation in controlled in vitro conditions. Toward these ends, human pluripotent stem cells (hPSCs), including human embryonic stem cells (hESCs) and human induced pluripotent stem cells (hiPSCs), have been widely studied due to their abilities to self-renew and differentiate into any cell type of the body. Recapitulation of low $O_2$ tensions during hPSC differentiation offers insights into embryonic development and in turn, may yield the generation of cells from a renewable source for therapeutic use.

Endothelial cells (ECs), which make up the inner lining of blood vessels, are in direct contact with blood, thus positioning them as the first responders to changes in $O_2$ levels. Indeed, previous studies have revealed that $O_2$ availability plays a vital role in EC differentiation from a variety of stem cell sources, including hESCs, mouse ESCs, human endothelial progenitor cells, human bone marrow CD133+ cells, and amniotic mesenchymal side population cells. Previous studies examining the influence of low $O_2$ tensions on EC differentiation from PSCs have relied on three-dimensional embryoid body differentiation—in which the local oxygen environment of each cell varies slightly according to the cell's position in the sphere as result of an oxygen gradient—or spontaneous differentiation from pluripotent cultures on feeder layers that may contribute to oxygen consumption. In a previous study, at was found that hPSCs can be induced to co-differentiate into early vascular cells (EVCs) using a step-wise differentiation protocol that employs a feeder-free monolayer culture and avoids an EB intermediate and sorting, thus enabling the study of the role of low $O_2$ in a controlled system. The EVCs were composed of ECs and pericytes, determined by their expression of vascular endothelial cadherin (VEcad) and platelet derived growth factor β (PDGFRβ), respectively.

Low oxygen environments have been shown to accelerate the generation of vascular precursors, characterized by the expression of Brachyury, Flk1, and BMP4, from mouse. Common markers of vascular precursors applicable to hPSCs include kinase domain receptor (KDR), CD34, and CD56. Furthermore, in response to changing DO levels, cells increase production of reactive oxygen species (ROS). With respect to ECs, ROS levels increase in response to hypoxia and reoxygenation. The role of ROS has also been implicated in cardiovascular differentiation of mouse ESCs to transduce mechanical signals. In ROS-induced conditions, hESCs were observed to differentiate into mesodermal and endodermal lineages. Here it is investigated whether exposure to 5% $O_2$ affected expression of early vascular markers as well as yielded ROS expression to transduce oxygen signals.

The role of low oxygen tension in vascular growth is further complicated by the fact that arterial and venous ECs are exposed to disparate oxygen tensions. Macroscopically, arterial ECs are subject to oxygenated blood flow, in contrast to venous ECs, which experience deoxygenated blood. Previous studies examining the role of low oxygen tension in EC fate specification has yielded confounding results. One study demonstrated that newborn mice exposed to moderate hypoxia (10% $O_2$) failed to express arterial markers but maintained vein-specific marker expression. However, endothelial progenitor cells acquired an arterial fate upon exposure to hypoxic conditions.

SUMMARY OF THE INVENTION

The present disclosure is based on the elucidation of the role of low oxygen environments on endothelial commitment from human pluripotent stem cells (hPSCs) through controlled differentiation environments. The data presented herein supports the finding that low oxygen tension during early stages of EVC derivation induces endothelial commitment and maturation through the accumulation of reactive oxygen species, thus highlighting the importance of regulating oxygen tensions during hPSC-vascular differentiation.

Accordingly, in one aspect, the present invention provides a method of generating early vascular cells (EVCs). The method includes culturing pluripotent stem cells (PSCs) under hypoxic conditions on a culture substrate in a growth medium suitable to induce differentiation of the PSCs, thereby generating EVCs.

In another aspect, the present invention provides a method of generating a bicellular population of vascular cells capable of self-organizing into vascular networks. The method includes: a) culturing pluripotent stem cells (PSCs) under hypoxic conditions on a first culture substrate in a first growth medium suitable to induce differentiation of the PSCs toward early vascular cells (EVCs); b) harvesting the cells of (a); and c) culturing the harvested cells optionally under hypoxic conditions on a second culture substrate in a second growth medium suitable to induce differentiation toward cells capable of self-organizing into vascular networks, thereby generating a population of cells capable of self-organizing into vascular networks.

In another aspect, the present invention provides a method of generating early endothelial cells (ECs). The method includes: a) culturing pluripotent stem cells (PSCs) under hypoxic conditions on a first culture substrate in a first growth medium suitable to induce differentiation of the PSCs toward early vascular cells (EVCs); b) harvesting the cells of (a); c) culturing the harvested cells optionally under hypoxic conditions on a second culture substrate in a second growth medium suitable to induce differentiation of the harvested cells toward ECs; and d) harvesting the cells of (c) and isolating VEcad+ cells, thereby generating ECs.

In another aspect, the present invention provides a substantially enriched population of cells generated by the method of the invention.

In another aspect, the present invention provides a pharmaceutical composition. The composition may include a population of cells generated by the method of the invention, and a pharmaceutically acceptable carrier.

In another aspect, the present invention provides a method of treating damaged tissue. The method includes contacting the damaged tissue with a population of cells generated by a method of the invention.

In another aspect, the present invention provides a method of making a conditioned medium composition. The method includes culturing pluripotent stem cells (PSCs) under hypoxic conditions on a culture substrate in a growth medium suitable to induce differentiation of the PSCs to early vascular cells (EVCs), thereby producing a composition having a soluble and a non-soluble fraction.

In another aspect, the present invention provides a composition including an isolated soluble or non-soluble fraction of conditioned medium generated by a method of the present invention.

DETAILED DESCRIPTION OF THE INVENTION

Figure 1A:
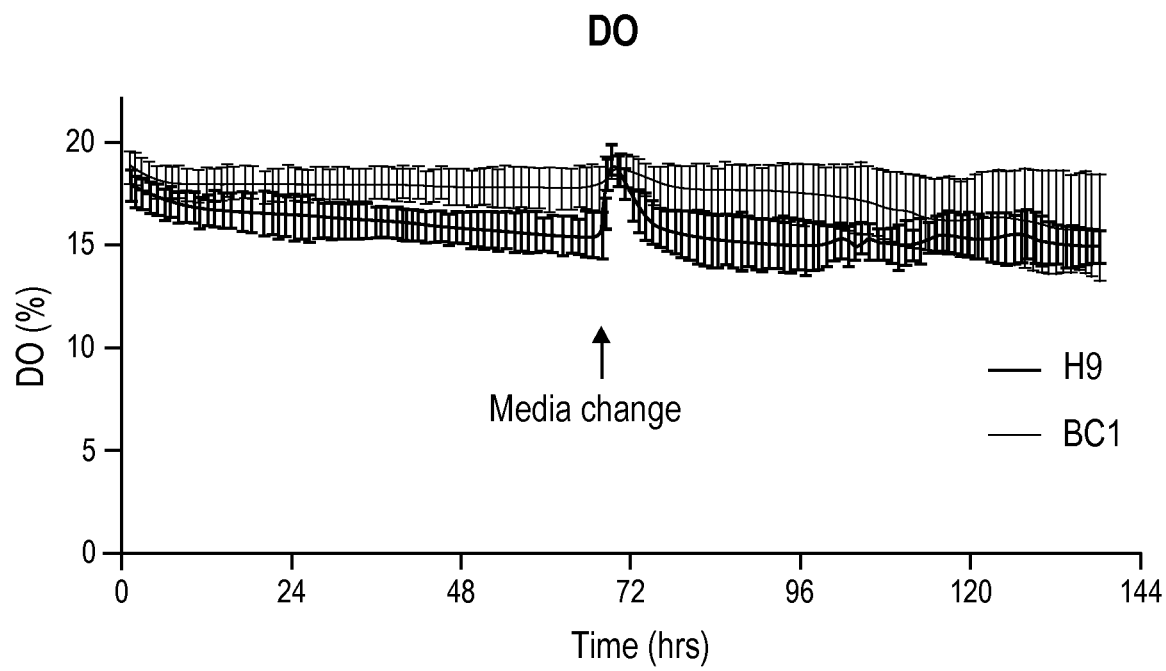
FIG. 1A-E. EVC differentiation in 5% $O_2$. DO measurements throughout feeder-free monolayer differentiation of hPSCs during (A) atmospheric conditions and (B) 5% $O_2$. After six days, differentiating cells were assessed for (C) cell growth and (D,E) expression of vascular progenitor markers via (D) flow cytometry and (E) RT-PCR.

The present invention is based on the determination that low oxygen tension during early stages of EVC derivation induces endothelial commitment and maturation through the accumulation of reactive oxygen species. The studies presented herein demonstrate the importance of low oxygen tension in EC differentiation in a controlled environment and importantly for the generation of ECs with clinical translatability.

A feeder-free, two-dimensional differentiation system was employed in which dissolved oxygen levels could be accurately monitored during hPSC differentiation toward early vascular cells (EVCs). It was found that oxygen uptake rate of differentiating hPSCs is lower in 5% $O_2$ compared to atmospheric conditions. EVCs differentiated in 5% $O_2$ had an increased VEcad expression with clusters of VEcad+ cells surrounded by PDGFRβ+ cells. Thus a bicellular population of cells resembling early vascular tissue was generated from a single cell source.

When the temporal effects of low oxygen differentiation environments were assessed, it was determined that low oxygen environments during the early stages of EVC differentiation enhance endothelial lineage commitment. EVCs differentiated in 5% $O_2$ exhibited an increased expression of VEcad and CD31 along with their localization to the membrane, enhanced lectin binding and acLDL uptake, rapid cord-like structure formation, and increased expression of arterial EC markers Inhibition of reactive oxygen species generation during the early stages of differentiation abrogated the endothelial inductive effects of the low oxygen environments.

Before the present compositions and methods are further described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

In various embodiments, the present invention involves methods for generating various types of cellular populations, such as bicellular populations having characteristics of early vascular tissue, as well as applications thereof. In particular, cells are generated from pluripotent stem cells (PSCs) via culture of the PSCs under hypoxic conditions in a suitable growth medium on a suitable surface, such as a two-dimensional or three-dimensional culture surface.

In particular, the PSCs are differentiated into early vascular cells (EVCs), early endothelial cells (ECs), pericytes and mixed populations thereof as described herein. Cellular differentiation is the process by which a less specialized cell becomes a more specialized cell type, often accompanied by dramatic changes in cellular characteristics, such as cell size, shape, membrane potential, metabolic activity, and responsiveness to signals. These changes are largely due to highly-controlled modifications in gene expression. Cell differentiation is thus a transition of a cell from one cell type to another and typically involves a switch from one pattern of gene expression to another.

As used herein, "differentiation" refers to a change that occurs in cells to cause those cells to assume certain specialized functions and to lose the ability to change into certain other specialized functional units. Cells capable of differentiation may be any of totipotent, pluripotent or multipotent cells. Differentiation may be partial or complete with respect to mature adult cells.

As discussed herein, various aspects of the present invention relate to in vitro methodology that results in conversion of cells of one differentiative state to that of another. Such methods encompass the application of culture and growth factor conditions in a defined and temporally specified fashion as described further herein. In various embodiments, the method of the present invention generates a cell population in which 10%, 20%, 30%, 40%, 50%, 60%, 70%, 80%, 90% or greater of the cells have an altered differentiative state. For example, the invention provides cell populations in which about 50-99%, 60-99%, 70-99%, 75-99%, 80-99%, 85-99%, 90-99% or 95-99% of the cells in culture are of a similar differentiative state. Further enrichment of the cell population for a particular cell type can be achieved by isolation and/or purification of altered cells from other cells in the population, for example by using reagents known in the art that specifically bind a particular cell type.

In one embodiment, the present invention provides a method of generating EVCs. The method includes culturing PSCs under hypoxic conditions on a culture substrate in a growth medium suitable to induce differentiation of the PSCs, thereby generating EVCs.

In another embodiment, the present invention provides a method of generating a bicellular population of vascular cells capable of self-organizing into vascular networks. The method includes: a) culturing PSCs under hypoxic conditions on a first culture substrate in a first growth medium suitable to induce differentiation of the PSCs toward EVCs; b) harvesting the cells of (a); and c) culturing the harvested cells optionally under hypoxic conditions on a second culture substrate in a second growth medium suitable to induce differentiation toward cells capable of self-organizing into vascular networks, thereby generating a population of cells capable of self-organizing into vascular networks.

In another embodiment, the present invention provides a method of generating early ECs. The method includes: a) culturing PSCs under hypoxic conditions on a first culture substrate in a first growth medium suitable to induce differentiation of the PSCs toward EVCs; b) harvesting the cells of (a); c) culturing the harvested cells optionally under hypoxic conditions on a second culture substrate in a second growth medium suitable to induce differentiation of the harvested cells toward ECs; and d) harvesting the cells of (c) and isolating VEcad+ cells, thereby generating ECs.

The cell types and compositions described herein can be produced from pluripotent cells, for example pluripotent stem cells (PSCs), such as induced pluripotent stem cells (iPSCs) or embryonic stem cells. As used herein, a "pluripotent cell" refers to a cell that can be maintained in vitro for prolonged, theoretically indefinite period of time in an undifferentiated state, that can give rise to different differentiated tissue types, i.e., vascular. The pluripotent state of such cultured cells can be confirmed by various methods, e.g., (i) confirming the expression of markers characteristic of pluripotent cells; (ii) production of chimeric animals that contain cells that express the genotype of the pluripotent cells; (iii) injection of cells into animals, e.g., SCID mice, with the production of different differentiated cell types in vivo; and (iv) observation of the differentiation of the cells (e.g., when cultured in the absence of feeder layer or LIF) into embryoid bodies and other differentiated cell types in vitro.

As used herein, "embryonic" refers to a range of developmental stages of an organism beginning with a single zygote and ending with a multicellular structure that no longer comprises pluripotent or totipotent cells other than developed gametic cells. In addition to embryos derived by gamete fusion, the term "embryonic" refers to embryos derived by somatic cell nuclear transfer. A preferred method for deriving cell populations as described herein utilizes iPSCs or embryonic stem cells as the starting cells for differentiation. The embryonic stem cells used in this method can be cells that originate from the morula, embryonic inner cell mass or those obtained from embryonic gonadal ridges. Human stem cells can be maintained in culture in a pluripotent state without substantial differentiation using methods that are known in the art. Such methods are described, for example, in U.S. Pat. Nos. 5,453,357, 5,670,372, 5,690,926 5,843,780, 6,200,806, 6,251,671 and U.S. patent application Ser. Nos. 12/082,028 and 12/629,813, the disclosures of which are incorporated herein by reference in their entireties.

As will be appreciated, a wide variety of two-dimensional and three-dimensional culture surfaces may be utilized. Any material and/or shape may be used that allows cells to attach to it (or can be modified to allow cells to attach to it).

In various embodiments, the culture surface may be a coated or uncoated cell culture plate comprising at least one sample well or vessel wherein the well or vessel has a base and at least one sidewall defining an opening, wherein the base of the vessel or well includes a zone for receiving cells. The vessel or well is not limited to any particular cross section and can be hexagonal, circular, semi-circular, ellipsoidal, rectangular, square or any other polygonal or curved shape.

In various embodiments the culture plate and sample well may be formed from a material which is compatible with cells; e.g., biocompatible. Suitable materials can include, glass, ceramics, metals, plastics, polymers including, but not limited to polystyrene, polycarbonate, polypropylene or polymeric thin films.

In various embodiments the culture plate may be coated with a suitable culture substrate. For example, the matrix can be formed from, but is not limited to, one or more of collagen, laminin, fibronectin, Matrigel™, agarose, or agar. In some embodiments, the substrate is formed from one or more of collagen, including, for example, type I collagen and/or type IV collagen, and fibronectin. Different concentrations of the substrate material may be utilized to alter the substrate properties.

Three-dimensional culture surfaces may also be utilized. Such surfaces may have interstitial spaces for attachment and growth of cells into a three dimensional tissue. The openings and/or interstitial spaces of the framework in some embodiments are of an appropriate size to allow the cells to stretch across the openings or spaces. Maintaining actively growing cells stretched across the framework appears to enhance production of the repertoire of growth factors responsible for the activities described herein. Any shape or structure that allows the cells to continue to replicate and grow for lengthy time periods may function to elaborate the cellular factors in accordance with the methods herein.

In some embodiments, the three dimensional culture surface is formed from polymers or threads that are braided, woven, knitted or otherwise arranged to form a framework, such as a mesh or fabric. The materials may also be formed by casting of the material or fabrication into a foam, matrix, or sponge-like scaffold. In other aspects, the three dimensional framework is in the form of matted fibers made by pressing polymers or other fibers together to generate a material with interstitial spaces. The three dimensional framework may take any form or geometry for the growth of cells in culture. Thus, other forms of the framework, as further described below, may suffice for generating the appropriate conditioned medium.

A number of different materials may be used to form the three-dimensional culture substrate. These materials include non-polymeric and polymeric materials. Polymers, when used, may be any type of polymer, such as homopolymers, random polymers, copolymers, block polymers, coblock polymers (e.g., di, tri, etc.), linear or branched polymers, and crosslinked or non-crosslinked polymers. Non-limiting examples of materials for use as scaffolds or frameworks include, among others, glass fibers, polyethylenes, polypropylenes, polyamides (e.g., nylon), polyesters (e.g., dacron), polystyrenes, polyacrylates, polyvinyl compounds (e.g., polyvinylchloride; PVC), polycarbonates, polytetrafluoroethylenes (PTFE; TEFLON), thermanox (TPX), nitrocellulose, polysaacharides (e.g., celluloses, chitosan, agarose), polypeptides (e.g., silk, gelatin, collagen), polyglycolic acid (PGA), and dextran.

In some embodiments, the three-dimensional culture substrate may be made of materials that degrade over time under the conditions of use. Biodegradable also refers to absorbability or degradation of a compound or composition when administered in vivo or under in vitro conditions. Biodegradation may occur through the action of biological agents, either directly or indirectly. Non-limiting examples of biodegradable materials include, among others, polylactide, polyglycolide, poly(trimethylene carbonate), poly(lactide-co-glycolide) (i.e., PLGA), polyethylene terephtalate (PET), polycaprolactone, catgut suture material, collagen (e.g., equine collagen foam), polylactic acid, or hyaluronic acid. For example, these materials may be woven into a three-dimensional framework such as a collagen sponge or collagen gel.

In other embodiments, where the cultures are to be maintained for long periods of time, cryopreserved, and/or where additional structural integrity is desired, the three dimensional framework may be comprised of a nonbiodegradable material. As used herein, a nonbiodegradable material refers to a material that does not degrade or decompose significantly under the conditions in the culture medium. Exemplary nondegradable materials include, as non-limiting examples, nylon, dacron, polystyrene, polyacrylates, polyvinyls, polytetrafluoroethylenes (PTFE), expanded PTFE (ePTFE), and cellulose.

In other embodiments, three-dimensional culture substrate is a combination of biodegradable and non-biodegradable materials. The non-biodegradable material provides stability to the three dimensional scaffold during culturing while the biodegradable material allows formation of interstitial spaces sufficient for generating cell networks that produce the cellular factors sufficient for therapeutic applications. The biodegradable material may be coated onto the non-biodegradable material or woven, braided or formed into a mesh. Various combinations of biodegradable and non-biodegradable materials may be used. An exemplary combination is poly(ethylene therephtalate) (PET) fabrics coated with a thin biodegradable polymer film, poly[D-L-lactic-co-glycolic acid), in order to obtain a polar structure.

As described herein, incubation of PSCs seeded onto the culture substrate is performed under hypoxic conditions, which is discovered to produce unique populations of cells under specific culture conditions. In some embodiments, initially seeded cells may be allowed to attach to the culture substrate in normoxic conditions. As used herein, hypoxic conditions are characterized by a lower oxygen concentration as compared to the oxygen concentration of ambient air (approximately 15%-21% oxygen). In one embodiment, hypoxic conditions are characterized by an oxygen concentration less than about 10%. In another embodiment hypoxic conditions are characterized by an oxygen concentration of about 1% to 10%, 1% to 9%, 1% to 8%, 1% to 7%, 1% to 6%, 1% to 5%, 1% to 4%, 1% to 3%, or 1% to 2%. In a certain embodiment, the system maintains about 5% oxygen within the culture vessel. Hypoxic conditions can be created and maintained by using a culture apparatus that allows one to control ambient gas concentrations, for example, an anaerobic chamber.

Incubation of cell cultures is typically performed in normal atmosphere with 15-21% oxygen and 5% $CO_2$ for seeding, at which point low oxygen cultures are put in an airtight chamber that is flooded with 5% $O_2$-95% $CO_2$—$N_2$ balance so that a hypoxic environment is created within the culture medium. For example, following the period of near atmospheric cultivation, the culture substrate may be incubated in a chamber designed for anaerobic cultivation that is purged with a gas mixture of approximately 5% $O_2$-95% $CO_2$—$N_2$ balance. Expended growth media is replaced with fresh media at atmospheric oxygen level through the culture period and after media is exchanged the culture substrate is place in the anaerobic chamber, the chamber is purged with 5% $O_2$-95% $CO_2$—$N_2$ balance then incubated.

Cultured cells may be harvested after incubation in hypoxic conditions. The cells may be cultured from about 2 to 12 days before harvesting, for example, between about 3 to 7 days, 4 to 7 days or 5 to 6 days. Optionally, after harvesting, the harvested cells may be reseeded on a second culture substrate that is the same or different than the first substrate and cultured for an additional length of time under either normoxic or hypoxic conditions. The duration of time the cells are cultured in second culture may be from about 2 to 12 days before harvesting, for example, between about 3 to 7 days, 4 to 7 days or 5 to 6 days. This process may be repeated until the desired cell population is achieved. During culture of the cells, the conditions may be changed from normoxic to hypoxic or from hypoxic to normoxic. Additionally, the cells may be harvested and isolated at any time during the first or second culture.

During the incubation period, the cultured cells grow and expand on the culture substrate. The growing cells may produce a myriad of growth factors, regulatory factors and proteins, some of which are secreted in the surrounding media, and others that are deposited on the support along with the cells.

Growth and regulatory factors can be added to the culture during incubation to induce differentiation of the cells to the desired cell type. For example, to produce EVCs, early ECs, pericytes and mixed populations thereof as described herein, growth factors such as vascular endothelial growth factor (VEGF) may be added at any point during the culture period. Additionally a transforming growth factor-β (TGF-β) inhibitor may be added, such as SB431542 (James et al.; *Nature Biotechnology.* 2010; 28:161-166) or an siRNA operable to inhibit TGF-β.

After inoculation of the culture substrate, the cell culture is incubated in an appropriate nutrient medium and incubation conditions that supports growth and differentiation of cells into the desire cell type. Many commercially available media such as Minimum Essential Medium (MEM) Alpha, Endothelial Growth Cell Media (ECGM), Dulbecco's Modified Eagles Medium (DMEM), RPMI 1640, Fisher's, Iscove's, and McCoy's, may be suitable for supporting the growth of the cell cultures. The medium may be supplemented with additional salts, carbon sources, amino acids, serum and serum components, vitamins, minerals, reducing agents, buffering agents, lipids, nucleosides, antibiotics, attachment factors, and growth factors. Formulations for different types of culture media are described in various reference works available to the skilled artisan (e.g., Methods for Preparation of Media, Supplements and Substrates for Serum Free Animal Cell Cultures, Alan R. Liss, New York (1984); Tissue Culture: Laboratory Procedures, John Wiley & Sons, Chichester, England (1996); Culture of Animal Cells, A Manual of Basic Techniques, 4th Ed., Wiley-Liss (2000)).

The growth or culture media used in any of the culturing steps of the present invention, whether under normoxic or hypoxic conditions, may include serum, or be serum free. In one embodiment, the media is MEM-alpha with 0.1 mM β-mercaptoethanol (β-ME) supplemented with 10% fetal bovine serum and optionally VEGF, a TGF-β inhibitor, or combination thereof. In another embodiment, the media is ECGM supplemented with 2% fetal bovine serum and optionally VEGF, a TGF-β inhibitor, or combination thereof. In one embodiment, the media is supplemented with Angiopoietin 1, TGFβ-1 or combination thereof.

In various embodiments VEGF is VEGF-A. In various embodiments, TGF-β inhibitor is SB431542. Additionally, the same media can be used for both hypoxic and aerobic cultivation. In various embodiments, the media is supplemented with greater than about 10, 20, 30, 40, 50, 60, 70, 80 ng/ml of VEGF. In various embodiments, the concentration of TGF-β inhibitor in the media is about 1, 2, 3, 4, 5, 6, 7, 8, 9, 10, 11, 12, 13, 14, 15, 20 or 25 μM or greater.

Incubation conditions are under appropriate conditions of pH, temperature, and gas (e.g., $O_2$, $CO_2$, etc) to maintain an hypoxic growth condition. In some embodiments, the cell culture can be grown in a monolayer on a two-dimensional substrate. In addition, the culture may be "fed" periodically to remove the spent media, depopulate released cells, and add new nutrient source.

During incubation of PSCs under hypoxic conditions, as compared to incubation under normal atmospheric oxygen concentrations, EVC derivation induces endothelial commitment and maturation through the accumulation of reactive oxygen species. The studies presented herein demonstrate the importance of low oxygen tension in EC differentiation in a controlled environment and importantly for the generation of ECs with clinical translatability.

In order to determine the amount of a particular type of a cell in a cell culture or cell population, a method of distinguishing this cell type from the other cells in the culture or in the population may be used. Accordingly, in one embodiment, the methods further relate to cell markers whose presence, absence and/or relative expression levels are specific for specific cell types. As used herein, "expression" refers to the production of a material or substance as well as the level or amount of production of a material or substance. Thus, determining the expression of a specific marker refers to detecting either the relative or absolute amount of the marker that is expressed or simply detecting the presence or absence of the marker. As used herein, "marker" refers to any molecule that can be observed or detected. For example, a marker can include, but is not limited to, a nucleic acid, such as a transcript of a specific gene, a polypeptide product of a gene, a non-gene product polypeptide, a glycoprotein, a carbohydrate, a glycolipid, a lipid, a lipoprotein or a small molecule.

For example, in one embodiment, the presence, absence and/or level of expression of a marker is determined by quantitative PCR (Q-PCR). Exemplary genetic markers include, but are not limited to c-MYC, KLF4, Sox2, Oct4, Nanog, Nestin, SSEA4, LIN28, Tra-1-60, Tra-1-81, VEGFR2/KDR, CD31, CD34, CD44, CD45, CD56, CD73, CD105, CD146, VEcad, PDGFRβ, ephrinB2, Nrp1, EphB4, Nrp2, SMMHC, peripherin, Tuj1, NG2, and other markers, which may be determined by quantitative Q-PCR. In another embodiment, immunohistochemistry is used to detect the proteins expressed by the above-mentioned genes. In another embodiment, Q-PCR and immunohistochemical techniques are both used to identify and determine the amount or relative proportions of such markers.

As such, it is possible to identify PSCs, EVCs, ECs, and pericytes as well as determine the proportion of each type of cell in a cell culture or cell population. For example, in one embodiment, PSCs express one or more of TRA-1-60, Tra-1-81, SSEA4, Oct4, Nanog, Sox2, Nestin, KLF4, LIN28 and c-MYC. In another embodiment, EVCs express one or more of VEcad, CD31, CD34, VEGFR2/KDR and CD56. In another embodiment, EVCs exhibit no or depleted expression of one or more of CD45, peripherin and Tuj1.

In another embodiment, pericytes express one or more of CD44, CD73, CD105, CD146, NG2 and PDGFRβ. In another embodiment, pericytes exhibit no or depleted expression of one or more of VEcad and CD31. In another embodiment, ECs express ephrinB2 and Nrp1, ephB4 and Nrp2, or VEcad and CD31. In another embodiment, EVCs, ECs and pericytes exhibit no or depleted expression of one or more of Tra-1-60 and Tra-1-81.

In one embodiment, a bicellular population of vascular cells including EVCs and pericytes is generated. As discussed further below, such bicellular populations are capable of self-organizing into vascular networks having a defined structure similar to early vascular tissue. It is notable that early vascular tissue may be generated from a heterogeneous cell population which provides several advantages over existing methods.

In another aspect, the present invention provides a method of making a conditioned medium composition. The method includes culturing PSCs under hypoxic conditions on a culture substrate in a growth medium suitable to induce differentiation of the PSCs to EVCs, early ECs and/or pericytes, thereby producing a composition having a soluble and a non-soluble fraction.

As used herein, "conditioned medium" includes both soluble and non-soluble fractions or any portion thereof. The non-soluble fraction includes those secreted proteins and biological components that are deposited on culture substrate along with adhered cells. The soluble fraction refers to culture media in which cells have been cultured and into which the cells have secreted active agent(s) and includes those proteins and biological components not deposited on the culture substrate. Both fractions may be collected, and optionally further processed, and used individually or in combination in a variety of applications as described herein.

As discussed throughout, the conditioned medium compositions of the present invention includes both soluble and non-soluble fractions or any portion thereof. It is to be understood that the compositions of the present invention may include either or both fractions, as well as any combination thereof. Additionally, individual components may be isolated from the fractions to be used individually or in combination with other isolates or known compositions.

Accordingly, in various aspects, conditioned medium compositions produced using the methods of the present invention may be used directly or processed in various ways, the methods of which may be applicable to both the non-soluble and soluble fractions. The soluble fraction, including the cell-free supernatant and media, may be subject to lyophilization for preserving and/or concentrating the factors. Various biocompatible preservatives, cryoprotectives, and stabilizer agents may be used to preserve activity where required. Examples of biocompatible agents include, among others, glycerol, dimethyl sulfoxide, and trehalose. The lyophilizate may also have one or more excipients such as buffers, bulking agents, and tonicity modifiers. The freeze-dried media may be reconstituted by addition of a suitable solution or pharmaceutical diluent, as further described below.

In other aspects, the soluble fraction is dialyzed. Dialysis is one of the most commonly used techniques to separate sample components based on selective diffusion across a porous membrane. The pore size determines molecular-weight cutoff (MWCO) of the membrane that is characterized by the molecular-weight at which 90% of the solute is retained by the membrane. In certain aspects membranes with any pore size is contemplated depending on the desired cutoff. Typical cutoffs are 5,000 Daltons, 10,000 Daltons, 30,000 Daltons, and 100,000 Daltons, however all sizes are contemplated.

In some aspects, the soluble fraction may be processed by precipitating the active components (e.g., growth factors) in the media. Precipitation may use various procedures, such as salting out with ammonium sulfate or use of hydrophilic polymers, for example polyethylene glycol.

In other aspects, the soluble fraction is subject to filtration using various selective filters. Processing the soluble fraction by filtering is useful in concentrating the factors present in the fraction and also removing small molecules and solutes used in the soluble fraction. Filters with selectivity for specified molecular weights include <5000 Daltons, <10,000 Daltons, and <15,000 Daltons. Other filters may be used and the processed media assayed for therapeutic activity as described herein. Exemplary filters and concentrator system include those based on, among others, hollow fiber filters, filter disks, and filter probes (see, e.g., Amicon Stirred Ultrafiltration Cells).

In still other aspects, the soluble fraction is subject to chromatography to remove salts, impurities, or fractionate various components of the medium. Various chromatographic techniques may be employed, such as molecular sieving, ion exchange, reverse phase, and affinity chromatographic techniques. For processing conditioned medium without significant loss of bioactivity, mild chromatographic media may be used. Non-limiting examples include, among others, dextran, agarose, polyacrylamide based separation media (e.g., available under various tradenames, such as Sephadex™, Sepharose™, and Sephacryl™).

In still other aspects, the soluble fraction is formulated as liposomes. The growth factors may be introduced or encapsulated into the lumen of liposomes for delivery and for extending life time of the active factors. As known in the art, liposomes can be categorized into various types: multilamellar (MLV), stable plurilamellar (SPLV), small unilamellar (SUV) or large unilamellar (LUV) vesicles. Liposomes can be prepared from various lipid compounds, which may be synthetic or naturally occurring, including phosphatidyl ethers and esters, such as phosphotidylserine, phosphotidylcholine, phosphatidyl ethanolamine, phosphatidylinositol, dimyristoylphosphatidylcholine; steroids such as cholesterol; cerebrosides; sphingomyelin; glycerolipids; and other lipids (see, e.g., U.S. Pat. No. 5,833,948).

The non-soluble or soluble fraction may be used directly without additional additives, or prepared as pharmaceutical compositions with various pharmaceutically acceptable excipients, vehicles or carriers. A "pharmaceutical composition" refers to a form of the soluble and/or non-soluble fractions and at least one pharmaceutically acceptable vehicle, carrier, or excipient. For intradermal, subcutaneous or intramuscular administration, the compositions may be prepared in sterile suspension, solutions or emulsions of the ECM compositions in aqueous or oily vehicles. The compositions may also contain formulating agents, such as suspending, stabilizing or dispersing agents. Formulations for injection may be presented in unit dosage form, ampules in multidose containers, with or without preservatives. Alternatively, the compositions may be presented in powder form for reconstitution with a suitable vehicle including, by way of example and not limitation, sterile pyrogen free water, saline, buffer, or dextrose solution.

In other aspects, non-soluble fractions are cryopreserved preparations, which are thawed prior to use. Pharmaceutically acceptable cryopreservatives include, among others, glycerol, saccharides, polyols, methylcellulose, and dimethyl sulfoxide. Saccharide agents include monosaccharides, disaccharides, and other oligosaccharides with glass transition temperature of the maximally freeze-concentrated solution (Tg) that is at least −60, −50, −40, −30, −20, −10, or 0° C. An exemplary saccharide for use in cryopreservation is trehalose.

In some embodiments, the non-soluble fraction, i.e., cells, deposited on the culture substrate may be collected and processed for administration.

In other embodiments, the non-soluble fraction may be concentrated and washed with a pharmaceutically acceptable medium for administration. Various techniques for concentrating the compositions are available in the art, such as centrifugation or filtering. Examples include, dextran sedimentation and differential centrifugation. Formulation of the three dimensional tissues may also involve adjusting the ionic strength of the suspension to isotonicity (i.e., about 0.1 to 0.2) and to physiological pH (i.e., pH 6.8 to 7.5). The formulation may also contain lubricants or other excipients to aid in administration or stability of the cell suspension. These include, among others, saccharides (e.g., maltose) and organic polymers, such as polyethylene glycol and hyaluronic acid. Additional details for preparation of various formulations are described in U.S. Patent Publication No. 2002/0038152, incorporated herein by reference.

As discussed above, the conditioned medium compositions of the present invention may be processed in a number of ways depending on the anticipated application and appropriate delivery or administration of the conditioned medium composition. For example, the compositions may be delivered as two or three-dimensional implants, or the compositions may be formulated for injection as described above. The terms "administration" or "administering" are defined to include an act of providing a compound or pharmaceutical composition of the invention to a subject in need of treatment. The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. The phrases "systemic administration," "administered systemically," "peripheral administration" and "administered peripherally" as used herein mean the administration of a compound, drug or other material other than directly into the central nervous system, such that it enters the subject's system and, thus, is subject to metabolism and other like processes, for example, subcutaneous administration.

The term "subject" as used herein refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

Accordingly, cells and cell populations generated using the method described herein, have numerous therapeutic and diagnostic applications. Such cells may be used for cell transplantation therapies in the treatment of numerous disease conditions.

In one aspect, the present invention provides a method of treating damaged tissue in a subject. The method includes contacting the damaged tissue with a population of cells generated by a method of the invention. Tissues that may be treated include, for example, vascular tissue. In embodiments, the tissue is vascular tissue of an ischemic wound, a diabetic wound or an ischemic wound.

As detailed in the examples and discussion that follow, it was hypothesized that physiological oxygen conditions direct endothelial fate of hPSCs. It was also speculated that by differentiating hPSCs in controlled conditions, precise elucidation of the role of low $O_2$ tension as a means to augment EC differentiation capacity and to direct EC fate specification could be obtained. Furthermore, an understanding was sought as to whether the influence of low $O_2$ was maintained in hiPSC differentiation, which has not been investigated previously. Toward this end, a fully genetically sequenced hiPSC line, BC1, was utilized which is also derived non-virally, making it a clinically-relevant modality with translational importance (Cheng et al., Cell Stem Cell. 2012; 10:337-344). The local $O_2$ microenvironment of the cells was measured under 5% $O_2$ and atmospheric differentiation conditions and the expression of early vascular markers under each condition was assessed. Next the phenotypes of EVCs under continuous 5% $O_2$ and control (atmospheric) conditions was evaluated. Finally, the role of ROS in the differentiation phenotypes was determined.

Because of their ability to differentiate into every cell type of the body and to self-renew indefinitely in culture, hPSCs represent an important channel toward the progress of tissue regenerative therapies owing to their potential to generate clinically-relevant numbers of any cell type of interest. Means to improve hPSC differentiation capacity will advance their clinical application toward repairing tissue in vivo or rebuilding tissue in vitro. Vital to these efforts is the regeneration of a functional blood supply to sustain tissue survival. Low oxygen tension is an important regulator in blood vessel growth. In the present disclosure, it is demonstrated that low oxygen environments augment endothelial differentiation from hPSCs.

When manipulating $O_2$ environments, the precise measurement of $O_2$ tension in the cellular microenvironment is critical in order to correlate cellular responses to $O_2$ availability. It has been previously demonstrated that, as a result of oxygen uptake by the cells, the $O_2$ microenvironment the cells experience varies from that in the macroenvironment. In a previous, as well as the current study, DO levels were monitored via a fluorescent quenching technique, in which a non-invasive sensor patch composed of a ruthenium-based metal complex is excited by an external fluorescence light source. As shown herein, it is confirmed that DO levels experienced by the cells are lower than that of the macroenvironment. Under atmospheric conditions, differentiating hPSCs experience DO levels closer to 15%. Contrastingly, hPSCs maintained in pluripotent culture under atmospheric conditions experience decreasing DO levels to ~5% $O_2$ along a three day culture period, as previously reported. These differences could be a result of the lower cell seeding density in the differentiation system and perhaps a slower proliferation rate. In 5% $O_2$ conditions, differentiating hPSCs actually experience DO levels close to 1% after three days in culture. These differences play a vital role in cellular responses as different pathways are activated under 5% $O_2$ versus 1% $O_2$.

Despite similar cell growth rates after six days, cells differentiated in 5% $O_2$ conditions demonstrated a lower OUR compared to control cells, concordant with previous findings that various cell types, including somatic and pluripotent cells, cultured under lower oxygen conditions exhibit lower OURs than cell cultured under atmospheric conditions. Six days differentiated cells did not express vascular progenitor markers CD34, KDR, or CD56 at the protein level. However, it is clear that the lower oxygen tension did affect mRNA expression of these vascular progenitor markers as RT-PCR revealed significantly increased expression of all three markers after six days under 5% $O_2$ conditions compared to control conditions. This discrepancy is likely due to the fact that though the low oxygen conditions are impacting the internal cellular machinery of the differentiating cells, six days may not be sufficient time to observe the differences at the protein level.

After 6 days of differentiation in either atmospheric or 5% $O_2$ conditions, cells were then subjected to a subsequent 6 days of differentiation in either condition. Indeed, continuous exposure to 5% $O_2$ for 12 days yielded EVCs with vastly different cell morphologies and cellular phenotypes compared to control EVCs. The low oxygen differentiation environment stimulated increased expression of EC markers VEcad and CD31 as well as their appropriate junctional localization. Low oxygen differentiation environments also yielded the generation of these derived ECs in discrete colonies throughout the culture, surrounded by PDGFRβ cells. This EC colony phenotype is reminiscent of an adult stem cell population, endothelial colony forming cells (ECFCs), known for their ability to differentiate to mature ECs.

Though the role of 5% $O_2$ in EC differentiation from hPSCs is implicated, an intriguing caveat to this generalization is that a low oxygen environment is especially critical during the early time points of differentiation. EVCs exposed to 5% $O_2$ only during the first half of differentiation exhibited two distinct cell morphologies, characterized as VEcad+ colonies surrounded by PDGFRβ+ pericytes. When alternately exposed to 5% $O_2$ only during the second half of differentiation, EVCs resembled control. The effect of early low oxygen tension is suggestive of embryonic differentiation in which the vascular system itself forms under hypoxic oxygen levels, which increase to more physiologic levels after the onset of flow.

Another important aspect of the low oxygen differentiation environment is its ability to accelerate EC maturation. EVCs differentiated in either continuous or primed 5% $O_2$ conditions exhibited appropriate membrane localization of CD31, in addition to VEcad. As previously reported, such robust membrane localization of VEcad or CD31 was only observed on sorted, subcultured VEcad+ cells on day 18 (i.e. mature EC derivatives). ECs in both primed and continuous EVCs also exhibited lectin binding and were able to uptake acLDL, a functionality associated with more mature EC phenotypes. Furthermore, continuous and primed EVCs demonstrated more rapid cord-like structure formation compared to control EVCs. Cord-like structures were observed as early as 4 hours after culture on Matrigel™ whereas a comprehensive network was not observed by EVCs until 24 hours. Control EVCs reached similar network formation capability on Matrigel™ with respect to mean tube length and mean tube thickness after 24 hours. Taken together, these data demonstrate that low oxygen differentiation conditions enhance EC commitment as exemplified by the boost in EC marker expression and functionalities.

The derivation of ECs specified for a particular function may yield more effective repair of dysfunctional or injured vasculature. That oxygen tension differs in arteries and veins warrants continued study of the role of this instructive signal in EC specification. The results presented herein reveal that a 5% $O_2$ differentiation environment promoted the derivation of arterial-like ECs as demonstrated by increased expression of arterial markers ephrinB2 and Nrp1. Because the ECs are co-derived with pericytes, it is speculated that the ECs may be more appropriately labeled as arteriole ECs. Previous studies have implicated a role for fluid shear stress or activation of cyclic AMP pathway in arterial specification from endothelial progenitor cells or mouse PSCs, respectively. Furthermore, it has been demonstrated that low oxygen conditions (~1% $O_2$) activate the Notch signaling pathway, which in turn upregulates arterial marker expression and represses venous marker expression in murine embryonic endothelial progenitor cells. Inhibition of Notch signaling under hypoxic conditions led to markedly reduced levels of arterial markers. Contrastingly, other studies demonstrate that moderate hypoxia (10% $O_2$) promoted vein-specific marker expression but not artery marker expression. The finding that low oxygen tension promotes arterial EC fate specification is in agreement with the former of these two studies, linking low oxygen tension to arterial fate. This appears to be the first study to make this connection in hPSC differentiation. The platform established here could be further leveraged to investigate these signaling pathways that drive specification more extensively.

Another common byproduct of hypoxic culture conditions is increased expression of VEGF, which acts upstream of Notch. Corroborating this finding, previous literature supports that arteriovenous specification may be regulated by distinct VEGF levels, indicating that higher VEGF concentrations yield arterial ECs whereas lower VEGF concentration yield venous EC. Intriguingly, was previously found that arterial EC differentiation from mouse PSCs under hypoxic conditions was independent of increases in VEGF.

To better understand the differences between 5% $O_2$ and atmospheric differentiated cells, the role of ROS on derivative phenotypes was examined. Increased ROS expression under 5% $O_2$ conditions was observed and it was confirmed that treatment with DPI diminished ROS generation. When DPI was added at the very beginning of differentiation, cell attachment and proliferation was diminished. This decreased cell viability may be due to the necessity of a basal level of ROS for cell survival in hPSCs, a dependency that has been demonstrated in other cell types. To assess whether ROS generation under 5% $O_2$ conditions was critical to the observed phenotypes of primed and continuous EVCs, the differentiating cells were treated with DPI from days three to six of 5% $O_2$ differentiation. The data indicated that VEcad and CD31 mRNA levels of DPI-treated EVCs were similar to or lower than that of control (i.e. atmospheric) EVCs, demonstrating that treatment with DPI abrogated the endothelial inductive effect of the low oxygen differentiation environments.

These studies demonstrate the importance of low oxygen tension in EC differentiation in a controlled environment and importantly for the generation of ECs with clinical translatability.

The following examples are provided to further illustrate the embodiments of the present invention, but are not intended to limit the scope of the invention. While they are typical of those that might be used, other procedures, methodologies, or techniques known to those skilled in the art may alternatively be used.

EXAMPLE 1

Materials and Methods

The following materials and methods were utilized throughout the Examples.

hPSC culture. Human ESC line H9 (passages 15 to 40; WiCell Research Institute, Madison, Wis.) and hiPSC line BC1 (Chou et al., *Cell Research.* 2011; 21:518-529; Cheng et al., *Cell Stem Cell.* 2012; 10:337-344) were cultured as previously described (Vo et al., *Stem Cell Rev.* 2010; 6:237-247; Wanjare et al., *Cardiovascular Research.* 2012). Cell lines were routinely examined for pluripotent markers using immunofluorescence staining and flow cytometry analysis for TRA-1-60, TRA-1-81, SSEA4 and Oct4.

Cell culture. ECFCs, HUAECs, and HUVECs were cultured as previously described (Kusuma et al. *The FASEB Journal*. 2012; 26:4925-4936). Briefly, ECFCs (Lonza, Walkersville, Md., USA), HUAECs and HUVECs (Promocell, Heidelberg, Germany were cultured in endothelial growth media-2 (EGM2, Lonza) containing 10% fetal bovine serum (FBS) on type I collagen (BD Biosciences, Franklin Lakes, N.J., USA). Media was changed every other day. Cells were passaged every three to four days with 0.05 trypsin/0.1% ethylenediaminetetraacetic acid (EDTA; Invitrogen, Carlsbad, Calif., USA) and maintained in a humidified incubator at 37° C. in a 5% $CO_2$ atmosphere.

Differentiation protocol. Human PSCs were collected through digestion with ethylenediaminetetraacetic acid (EDTA; Promega, Madison, Wis.), separated into an individual cell suspension using a 40-μm mesh strainer (BD Biosciences), and plated onto collagen IV (Trevigen) coated plates at a concentration of $5 \times 10^4$ cells/cm². Cells were cultured in a differentiation medium composed of alpha-MEM (Invitrogen Carlsbad, Calif.), 10% FBS (Hyclone) and 0.1 mM β-mercaptoethanol (β-ME) as previously described (Kusuma et al. *Proceedings of the National Academy of Sciences*. 2013). For continuous and primed 5% $O_2$ conditions, a previously published protocol was modified (Abaci et al., *American Journal of Physiology—Cell Physiology*. 2010; 298:C1527-C1537). Cells were allowed to attach in normoxic (21% $O_2$) conditions for 4 hours, and then subjected to physiologic (5% $O_2$) conditions in a hermetically sealed chamber. 5% oxygen concentration was achieved by flushing the chamber with a 5% $O_2$-5% $CO_2$—$N_2$ balance for 3 min at 3 psi and three times every thirty minutes. Humidity was maintained in the chamber by inclusion of sterile water in a petri dish at the bottom of the chamber. The chamber was flushed and media was changed after 3 days to avoid slight changes in control oxygen concentrations due to oxygen consumption by the cells and to replenish nutrients to support cell growth. On day 6, differentiated cells were collected through digestion with TrypLE™ (Invitrogen), separated with a 40-μm mesh strainer, and seeded at a concentration of $1.25 \times 10^4$ cells/cm² on collagen-type-IV-coated plates in endothelial cell growth media (ECGM) (PromoCell, Heidelberg, Germany) supplemented with 2% FBS, 50 ng/ml VEGF, and 10 μM SB431542 (Tocris) for an additional 6 days. For continuous 5% $O_2$ conditions, cells were allowed to attach for 4 hours in normoxic conditions, and then subjected to 5% $O_2$ conditions as described above. Media was changed and where appropriate, the chamber was flushed, every 3 days.

DO measurements. Dissolved oxygen (DO) levels were measured as previously described (Abaci et al., *American Journal of Physiology—Cell Physiology*. 2010; 298:C1527-C1537; Abaci et al., *Biomedical Microdevices*. 2012; 14:145-152; Abaci et al., *Biotechnology and Applied Biochemistry*. 2012; 59:97-105; Abaci et al., *American Journal of Physiology—Cell Physiology*. 2011; 301:C431-C440). Briefly, DO was measured noninvasively, using a commercially available sensor dish reader (SDR; PreSens GmbH, Regensburg, Germany) capable of reading DO levels from an immobilized fluorescent patch affixed to the bottom of culture plate (Oxo-Dish OD-6; PreSens). The plates are sterilized and calibrated by the manufacturer for consistency in measurements. The dishes were then coated with collagen IV in a manner identical to dishes without sensor patches; all measurements were performed in a controlled environment within an incubator at 37° C., and were taken every five minutes. Collected data were exported for analysis into Excel™ (Microsoft, Inc., Redmond, Wash.) and GraphPad Prism™ (4.02, GraphPad Software™, San Diego, Calif.).

Calculation of OUR. The OUR is calculated based on several key assumptions as previously (Abaci et al., *American Journal of Physiology—Cell Physiology*. 2010; 298: C1527-C1537): (1) equilibrium is achieved at the liquid-gas interface, (2) oxygen concentration remains steady, (3) oxygen diffusivity in medium is similar to that in water, and (4) population changes are slow. From these assumptions, the OUR is calculated by:

$$OUR = D_{O_2} \frac{(C^* - C_0)}{h\varphi}$$

where $D_{O2}$ is the oxygen diffusivity in water ($3.35 \times 10^{-5}$ cm²/s), $C^*$ is the oxygen at the bottom surface in mol/cm³, $C_0$ is the concentration of oxygen in the gas phase in mol/cm³, h is the height of the liquid in the well in cm, and $\varphi$ is the number of cells per cm². (For the complete derivation, please refer to (Abaci et al., *American Journal of Physiology—Cell Physiology*. 2010; 298:C1527-C1537).

Flow cytometry. Flow cytometry was performed as previously described (Kusuma et al., *The FASEB Journal*. 2012; 26:4925-4936). Briefly, cells were incubated with FITC- or PE-conjugated antigen specific antibodies for markers outlined in the text. All analyses were done using corresponding isotype controls. Forward-side scatter plots were used to exclude dead cells. User guide instructions were followed to complete the flow cytometry analysis via Cyflogic™ v1.2.

Real-time quantitative RT-PCR. Two-step reverse transcription polymerase chain reaction (RT-PCR) was performed on differentiated and undifferentiated (day 0) hPSCs as previously described in accordance with Applied Biosystems manufacturer instructions (Kusuma et al., *The FASEB Journal*. 2012; 26:4925-4936). For each primer set (CD34, KDR, CD56, VEcad, CD31, ephrinB2, EphB4, Nrp1, Nrp2), the comparative computerized tomography method (Applied Biosystems, Foster City, Calif.) was used to calculate the amplification differences between different samples. The values for experiments were averaged and graphed with standard deviations.

Immunofluorescence. Cells were prepared for immunofluorescence as previously described (Kusuma et al., *The FASEB Journal*. 2012; 26:4925-4936). Briefly, fixed cells were blocked in 1% BSA, treated with 0.1% Triton-X™ (Sigma-Aldrich, St. Louis, Mo.), and incubated with the antigen specific antibodies for the markers outlined in the text, followed by an appropriate secondary, and DAPI (Roche Diagnostics). The immunolabeled cells were examined using a fluorescent microscope (Olympus BX60).

Matrigel™. Cord formation on Matrigel™ was assessed as previously described (Vo et al., *Stem Cell Rev*. 2010; 6:237-247; Kusuma et al., *Proceedings of the National Academy of Sciences*. 2013). Briefly, Matrigel™ was cast into 16 well chamber slides (Lab-Tek). After polymerization, 20,000 cells were seeded per well in 50 ng/ml VEGF media. Cord formation was observed after 4, 12 and 24 h. Quantification was performed using the Angiogenesis Tube Formation application module in Metamorph™.

Arteriovenous fate determination. To assess fate specification, RT-PCR analysis was performed on control ECFCs, HUAECs, and HUVECs, and derived control, primed, and continuous EVCs. All data were normalized to expression by ECFCs. The ratio of ephrinB2 to EphB4 and Nrp1 to Nrp2 was calculated. The natural log of the ratio was taken and graphed versus cell type.

ROS detection and inhibition. Previously published protocols were followed to detect and inhibit ROS production (Abaci et al., *American Journal of Physiology—Cell Physiology.* 2011; 301:C431-C440). For ROS detection, the culture media was replaced with 10 µM 2',7'-dichlorodihydrofluorescein diacetate (H2-DCFDA) (Invitrogen) in PBS and incubated for 30 min at 37° C. Samples were washed with PBS three times prior to imaging. For ROS inhibition, cells were treated with diphenyleneiodonium (DPI) (Sigma-Aldrich) at a concentration of 10 µM.

Graphs and Statistics. All analyses were performed in triplicate samples for n=3 at least. Real-time RT-PCR were also performed on triplicate samples (n=3) with triplicate readings. One Way ANOVA with Bonferroni post-hoc test were performed to determine significance (GraphPad Prism™ 4.02).

EXAMPLE 2

DO Measurements and Oxygen Uptake Rate

Three classes of hypoxia have been described in correlation with the oxygen concentration in the blood: moderate hypoxia (~5% $O_2$), severe hypoxia (~1% $O_2$), and anoxia (no $O_2$) (Paternotte et al., *Bio-Medical Materials and Engineering.* 2008; 18:295-299). Moderate hypoxia corresponds to physiologic oxygen tension, or the concentration of oxygen typically found in blood vessels. Alternatively, severe hypoxia is found within certain tissues, the developing embryo, and in tumors; anoxia arises from complete lack of blood flow and has been suggested to be present in the bone marrow niche (Ma et al., *Biotechnol Prog.* 2009; 25:32-42; Kumar et al., *Food Bioprod Process.* 2004; 82:105-116) Previous studies have reported that prolonged differentiation in 1% $O_2$ conditions yielded cell death and low quality RNA (Prado-Lopez et al., *Stem Cells.* 2010; 28:407-418); thus, a 5% $O_2$ environment was focused on as a representative of physiologically relevant conditions.

In this study, hPSCs were differentiated in feeder-free monolayer cultures following the established protocol (Kusuma et al., *Proceedings of the National Academy of Sciences.* 2013; 110:12601-12606). Measuring dissolve oxygen (DO) levels during the first six days of differentiation to determine the oxygen uptake rate (OUR) was done first. Towards this end, hPSCs were dissociated into a single cell suspension and seeded on a collagen IV substrate with oxygen sensor patches affixed to the bottom. Using this system, it is possible to measure DO levels precisely at the cells' microenvironment (Abaci et al., *Biomedical microdevices.* 2012; 14:145-152; Abaci et al., *Biotechnology and applied biochemistry.* 2012; 59:97-105; Abaci et al.; *American Journal of Physiology—Cell Physiology.* 2010; 298: C1527-C1537; Abaci et al.; *American journal of physiology. Cell physiology.* 2011; 301:C431-440). DO levels were measured every 30 minutes for six days, and changed media on the third day. Under atmospheric conditions (approximately 20% $O_2$), DO levels decreased to ~15% $O_2$ for both hESC-H9 and hiPSC-BC1 differentiating cells (FIG. 1A; for ease of visualization, measurements every 60 minutes are presented on the graph).

Figure 1B:
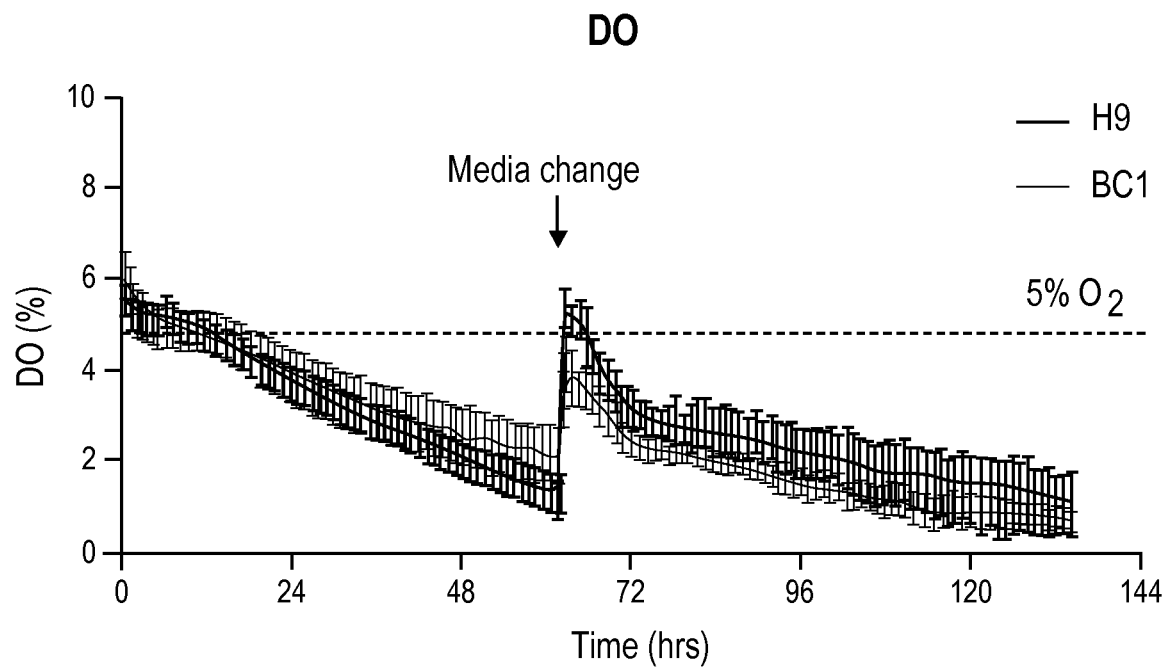
Figure 1C:
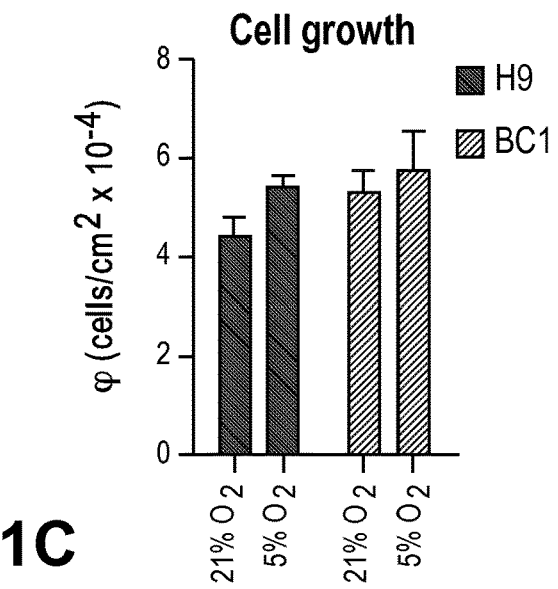

To obtain 5% $O_2$ conditions, differentiation occurred in a hermetically sealed chamber that was flushed with a nitrogen/carbon dioxide/oxygen mixture to obtain 5% $O_2$ conditions prior to DO measurements. Under these conditions, oscillations in DO levels were initially detected (data not shown). These fluctuations were attributed to the low temperature of the gas mixture used to flush the chamber to obtain a 5% $O_2$ environment. Thus, the measurements begin once the temperature within the chamber is constant (i.e. after 2.5 hours). It was found that DO levels of differentiating cultures decreased to approximately 1% $O_2$ over the first six days of 5% $O_2$ differentiation (FIG. 1B). DO levels did not appear to reach equilibrium after 3 days, as evidenced by the downward sloping trend over the first 3 days. Over the next 3 days, DO levels decreased in a gradual fashion and reached a steady state on the sixth day. After 6 days, cell density was not significantly different between the two hPSC lines or variable oxygen tensions (FIG. 1C).

The difference in the oxygen partial pressure in the chamber and the DO level measured by the sensors allows calculation of the oxygen gradient. Using this gradient and taking into account the cell growth after six days, the OUR per cell can also be calculated (please see Example 1). The difference in OURs between hPSC lines were not significant; however, the OUR of cells differentiated in atmospheric conditions was significantly greater than that in 5% $O_2$ conditions for each cell line (Table 1). These findings agree with previously reported data that demonstrated the OUR of hPSC cultures under atmospheric conditions was greater than that in lower oxygen conditions (Abaci et al.; *American Journal of Physiology—Cell Physiology.* 2010; 298:C1527-C1537).

TABLE 1

Table 1. Calculation of OUR. $xO2$ is molar fraction of oxygen in the liquid

| Control | | |
|---|---|---|
| $P_{O2}$, % | 21 | 5 |
| $x_{O2}$ | $4 \times 10^{-6}$ | $9.6 \times 10^{-7}$ |
| C*, µM | 224 | 53 |
| H9 | | |
| $C_0$, µM | 159.5 ± 9.2 | 8.3 ± 3.1 |
| $P_{O2}$, % | 14.9 | 0.8 |
| OUR, pmol/s per $10^6$ cells | 73.0 ± 16.1 | 41.3 ± 4.2 |
| BC1 | | |
| $C_0$, µM | 168.8 ± 16.7 | 10.8 ± 1.2 |
| $P_{O2}$, % | 15.8 | 1.0 |
| OUR, pmol/s per $10^6$ cells | 51.7 ± 17.9 | 36.9 ± 5.3 |

EXAMPLE 3

Assessment of Early Vascular Marker Expression

Figure 1D:
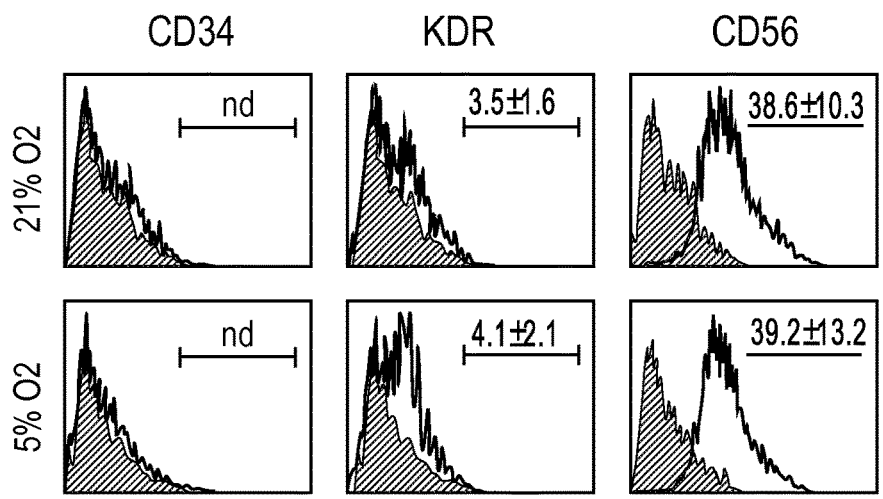
Figure 1E:
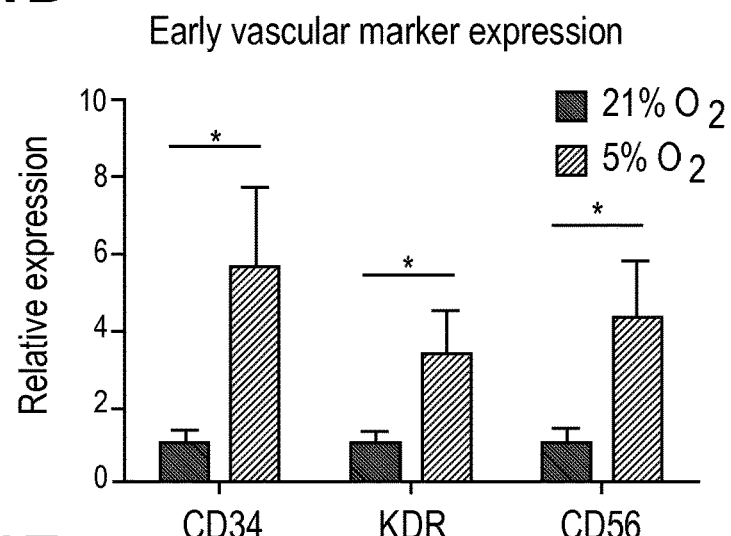

After six days of differentiation in either atmospheric or 5% $O_2$ conditions, the expression of early vascular markers by the differentiated cells was assessed. Flow cytometry revealed no difference in protein expression of KDR, CD34, CD56 between the differentiation conditions (FIG. 1D). However, RT-PCR analysis revealed that CD34, KDR, and CD56 expression is significantly increased in 5% $O_2$-differentiated cells compared to control differentiation (FIG. 1E).

EXAMPLE 4

Effect of 5% $O_2$ Environment on Endothelial Differentiation

Figure 2A:
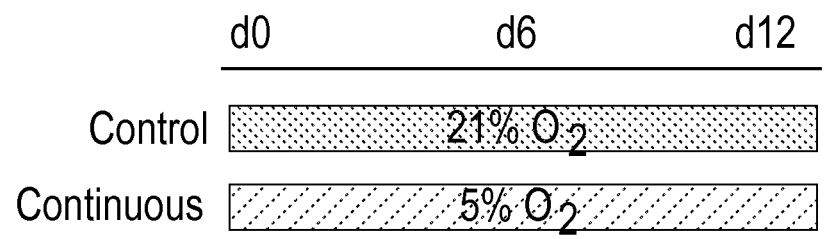
FIG. 2A-E. Effect of 5% $O_2$ on endothelial differentiation. (A) Schematic of manipulated oxygen environments. Comparison of control and continuous 5% $O_2$ conditions demonstrated by (B) light microscopy images (arrows: elongated cell bundles; arrowheads: cobblestone area-forming cells; scale bar is 100 μm), (C) flow cytometry for VEcad expression, and (D, E) immunofluorescence images of VEcad and PDGFRβ. Scale bar in D is 500 μm; scale bar in E is 100 μm.
Figure 2B:
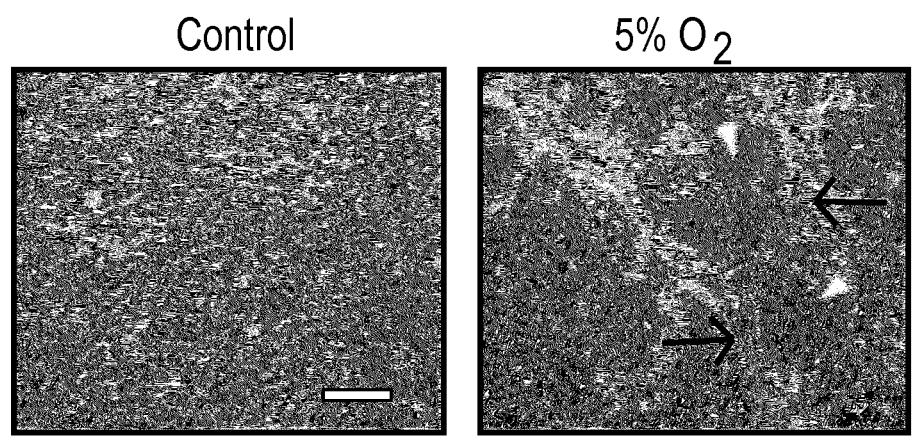
Figure 2C:
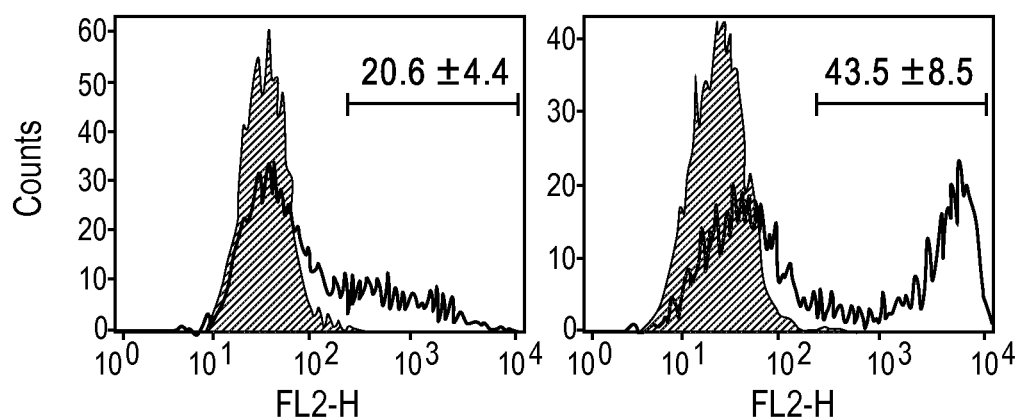

Next, the effect of variable oxygen conditions on the bicellular EVCs was assessed. The EVCs derived in continuous 5% $O_2$ tension were compared to control conditions (FIG. 2A). Control conditions were differentiating cells exposed to atmospheric conditions for all 12 days (control EVCs (Kusuma et al., *Proceedings of the National Academy of Sciences*. 2013; 110:12601-12606)). In continuous 5% $O_2$ conditions, cells were exposed to a 5% $O_2$ environment for all 12 days of differentiation. Light microscopy images revealed drastic morphological differences in the cell derivatives (FIG. 2B). EVCs differentiated in control conditions appeared spread with no visible organization. Remarkably, EVCs differentiated in continuous 5% $O_2$ conditions adopted an organized structure and exhibited two distinct morphologies: elongated cells bundles (arrows) and cobblestone area-forming cells (arrowheads). Flow cytometry analysis of these derivatives revealed that 5% $O_2$-differentiated EVCs exhibited greater VEcad expression compared to control conditions (FIG. 2C; $p<0.05$).

Figure 2D:
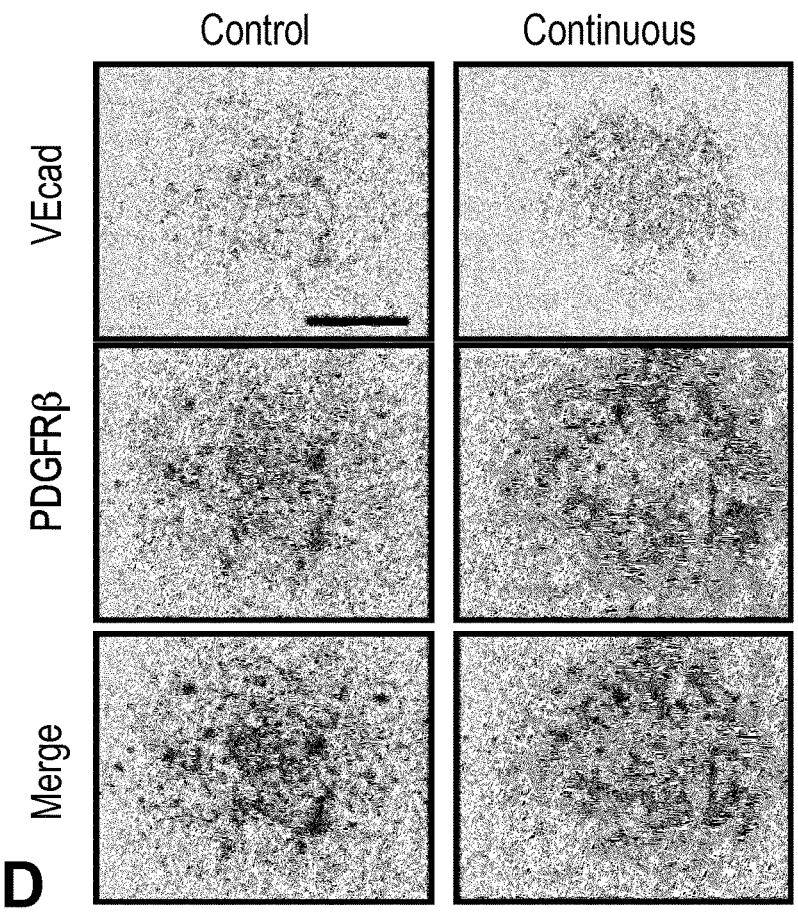
Figure 2E:
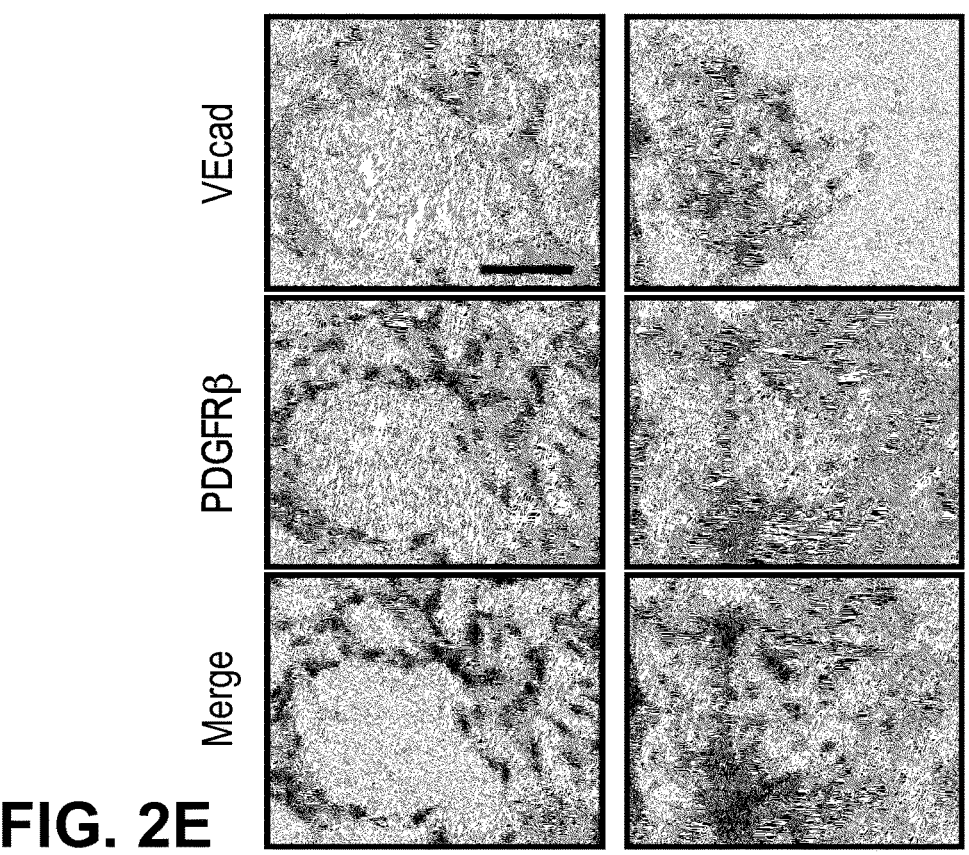

Immunofluorescent staining revealed further differences between the EVCs. Some VEcad expression in control EVCs was membrane localized, but most was intracellular (FIG. 2D,E). Control EVCs exhibited PDGFRβ expression localized to the nucleus, most likely as a result of non-specific binding. Contrastingly, immunofluorescent images uncovered a unique organization of two distinct populations of VEcad$^+$ and PDGFRβ$^+$ cells in 5% $O_2$ EVCs (FIG. 2D). VEcad$^+$ clusters were observed to be surrounded by PDGFRβ$^+$ pericytes. Moreover, VEcad expression was appropriately localized to the cellular membrane in EVCs derived via continuous 5% $O_2$ environments (FIG. 2E). PDGFRβ expression in 5% $O_2$ EVCs was largely expressed in cells' cytoplasm.

EXAMPLE 5

Effects of Temporal Low Oxygen Differentiation Environments

Figure 3A:
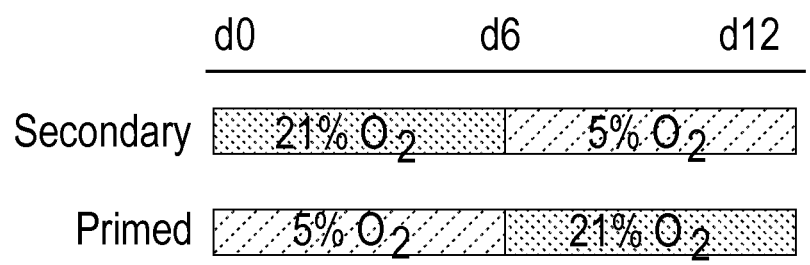
FIG. 3A-E. Effect of temporal 5% $O_2$ differentiation conditions. (A) Schematic of manipulated oxygen environments. (B) RT-PCR analysis of VEcad and CD31 expression of EVCs differentiated under the four studied oxygen conditions. Comparison of secondary and primed 5% $O_2$ conditions demonstrated by (C) light microscopy images (arrows: elongated cell bundles; arrowheads: cobblestone area-forming cells; scale bar is 100 μm) and (D) flow cytometry for VEcad expression. (E) Immunofluorescence images of primed 5% $O_2$ EVCs for VEcad and PDGFRβ. Scale bar for left column is 500 μm; scale bar for right column is 100 μm. *$P<0.05$; $P<0.01$; *$P<0.001$.
Figure 3B:
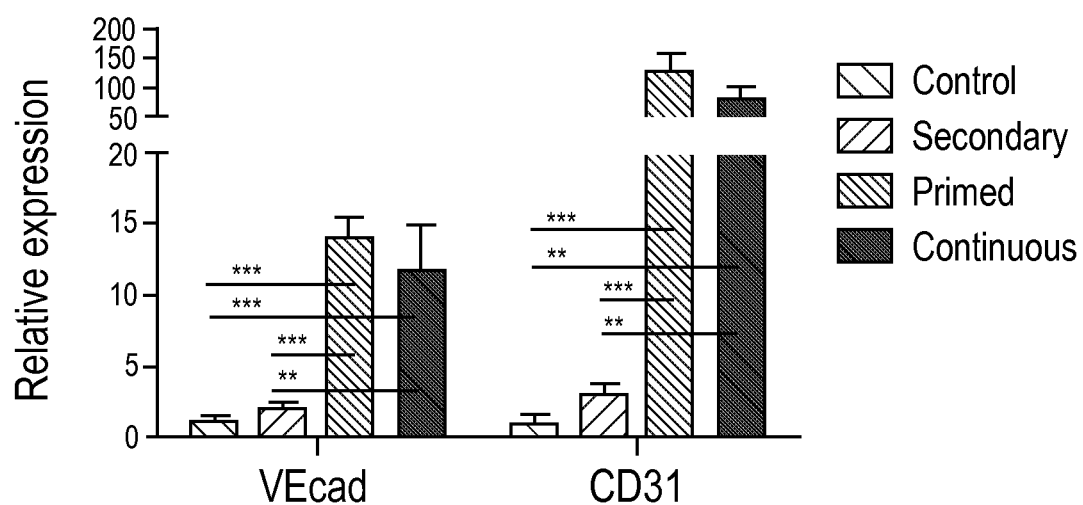
Figure 3C:
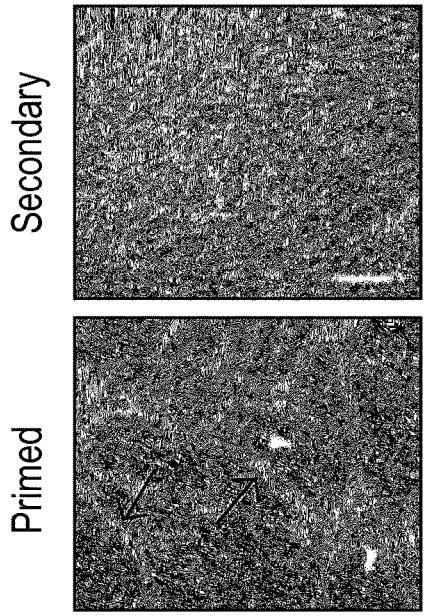
Figure 3D:
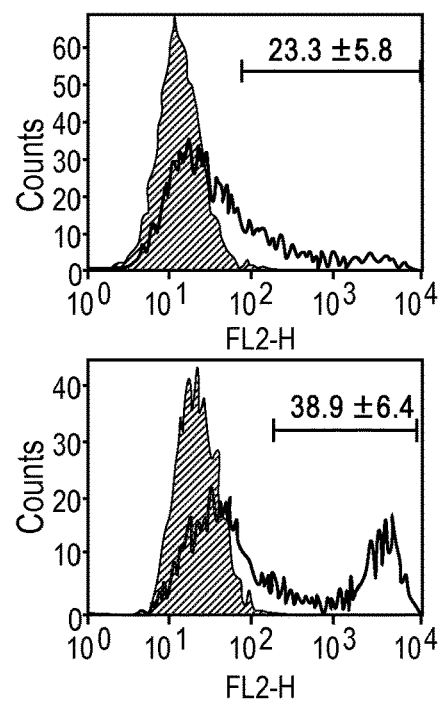
Figure 3E:
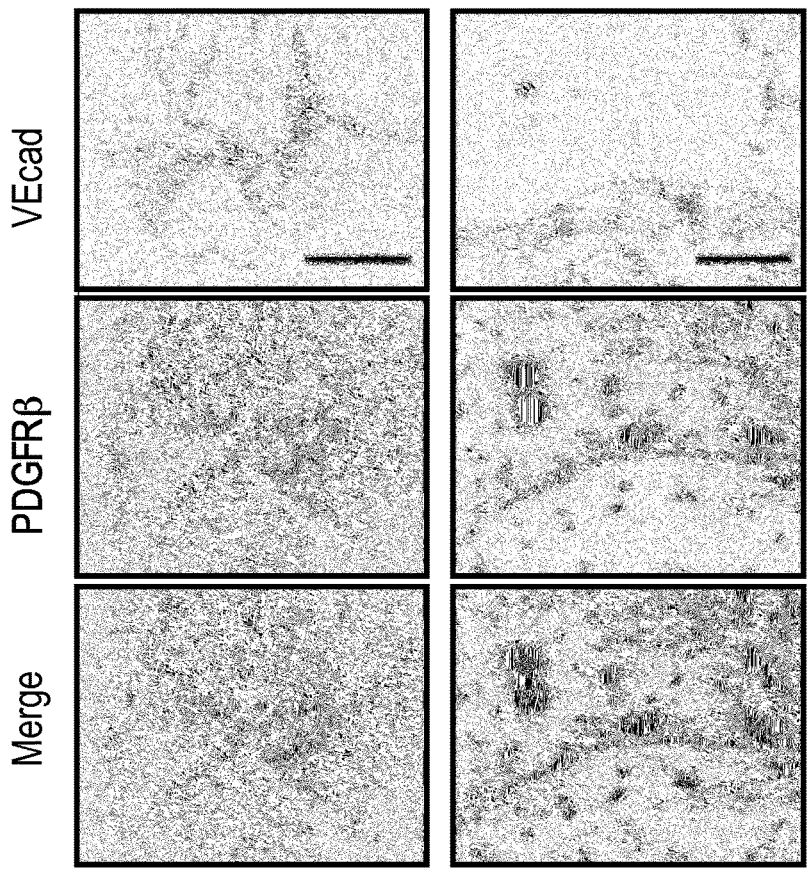

To determine whether low oxygen environments play a role in a temporal manner, the effect of 5% $O_2$ environments over the first half of differentiation was compared to the effect of 5% $O_2$ environments over the second half of differentiation (FIG. 3A). In the secondary 5% $O_2$ conditions, cells were exposed to control (i.e. atmospheric) conditions for the first six days of differentiation followed by six days in 5% $O_2$ conditions. Conversely, in the 5% $O_2$ primed condition, cells were exposed to a 5% $O_2$ environment for the first six days of differentiation followed by six days in control conditions. mRNA levels of VEcad and CD31 were found to be significantly increased in continuous or primed 5% $O_2$ conditions compared to control conditions (FIG. 3B). Interestingly, when cells were alternately cultured in secondary 5% $O_2$ conditions, VEcad and CD31 mRNA expression levels were similar to that of control conditions. Correspondingly, light microscopy revealed that secondary 5% $O_2$ EVCs lacked any organization (similar to control conditions) whereas primed 5% $O_2$ EVCs resembled continuous 5% $O_2$ EVCs with an organization composed of elongated cell bundles (arrows) and cobblestone area forming cells (arrowheads) (FIG. 3C). Flow cytometry for VEcad expression confirmed that primed 5% $O_2$ EVCs had significantly greater VEcad protein expression compared to secondary 5% $O_2$ EVCs (FIG. 3D). In fact, VEcad expression by primed 5% $O_2$ EVCs was similar to that by continuous 5% $O_2$ EVCs (from FIG. 2C). Finally, it was confirmed that primed 5% $O_2$ EVCs also displayed clusters of VEcad+ cells surrounded by PDGFRβ+ pericytes (FIG. 3E, left), with appropriately localized VEcad and PDGFRβ (FIG. 3E, right). Altogether, these data demonstrate that low oxygen conditions during the early stages of differentiation enhance endothelial lineage commitment

EXAMPLE 6

Effect of 5% $O_2$ on Endothelial Fate

Figure 4A:
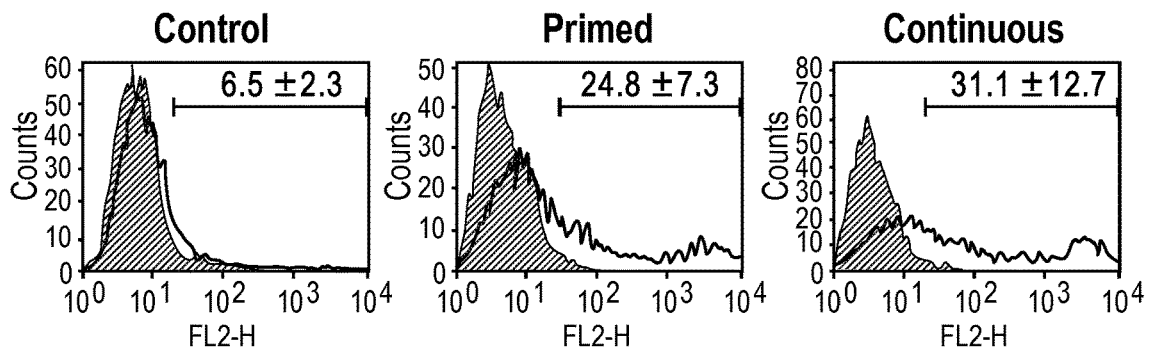
FIG. 4A-G. EC differentiation under varying oxygen conditions. (A) Flow cytometry analysis of CD31 expression. (B-D) Immunofluorescent images of (B) CD31 (scale bar is 200 μm; inserts are high magnification of boxed region) (C) lectin (scale bar in i, ii are 500 μm, 200 μm, respectively; second column is high magnification image of boxed area), (D) uptake of acLDL (scale bar is 200 μm) in EVCs derived under primed or continuous 5% $O_2$ conditions compared to control and (E, F) assessment of cord formation over 24 h (scale bar is 500 μm). (G) Quantification of arterial and venous marker expression by control, primed, and continuous EVCs compared to control HUAECs and HUVECs. Data were normalized to ECFC expression levels. *$P<0.05$; $P<0.01$; *$P<0.001$.
Figure 4B:
Figure 4C:
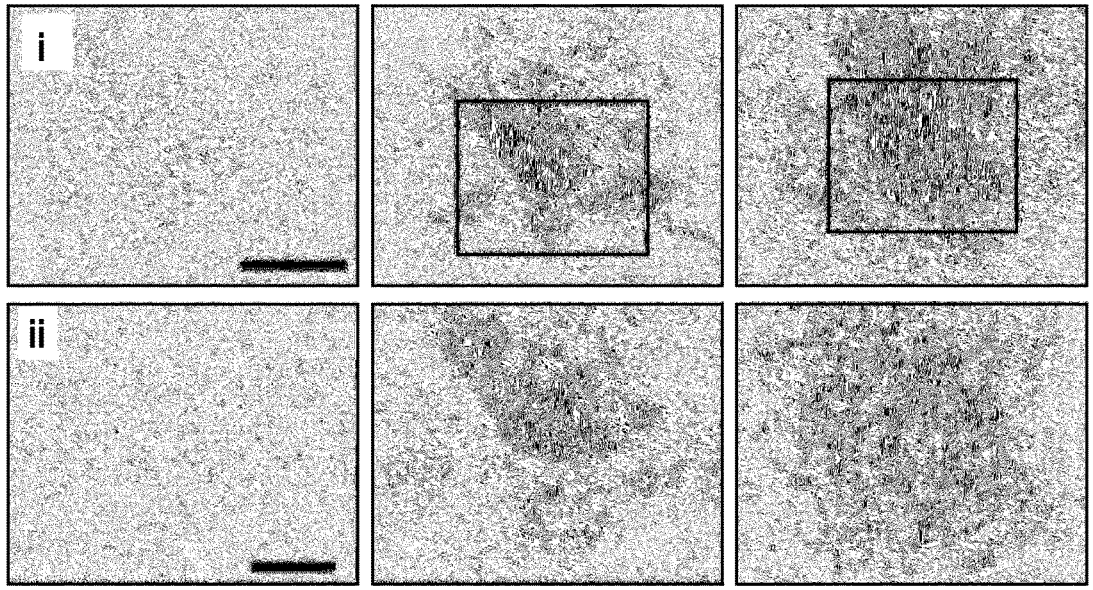

As the data suggested augmented EC differentiation, EC characteristics were further investigated. For these studies, control EVCs were compared to primed and continuous 5% $O_2$ EVCs. Flow cytometry analysis revealed significantly augmented CD31 expression under either 5% $O_2$ condition (FIG. 4A; $p<0.05$). Immunofluorescent assessment of cultures corroborated this result and revealed the expression of clusters of cells expressing CD31 appropriately localized to the cell membrane (FIG. 4B). Also increased lectin binding was observed in EVCs differentiated under either primed or continuous 5% $O_2$ conditions (FIG. 4C). Lectin was not expressed in control EVCs; however, clusters of lectin+ cells could be observed under both 5% $O_2$ conditions (FIG. 4C).

Figure 4D:
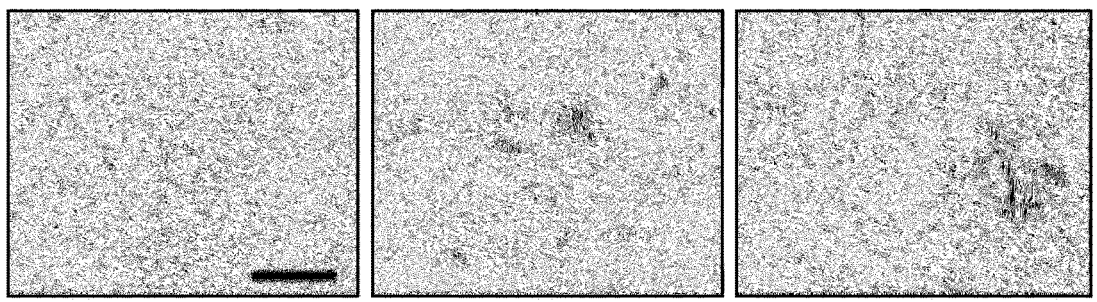

As part of the body's cholesterol metabolism, ECs are able to incorporate acetylated low density lipoprotein (acLDL). When the ability for the three classes of EVCs to endocytose acLDL in vitro was examined, it was determined that primed and continuous EVCs were able to uptake acLDL again following a clustered phenotype (FIG. 4D). No acLDL uptake in control EVCs was detected.

Figure 4E:
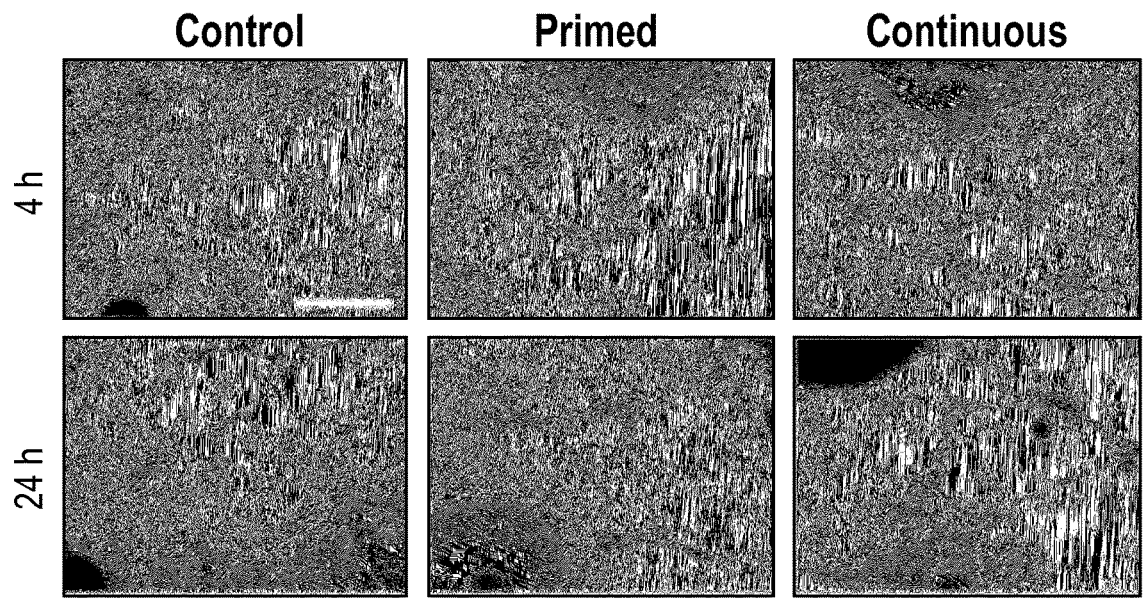
Figure 4F:
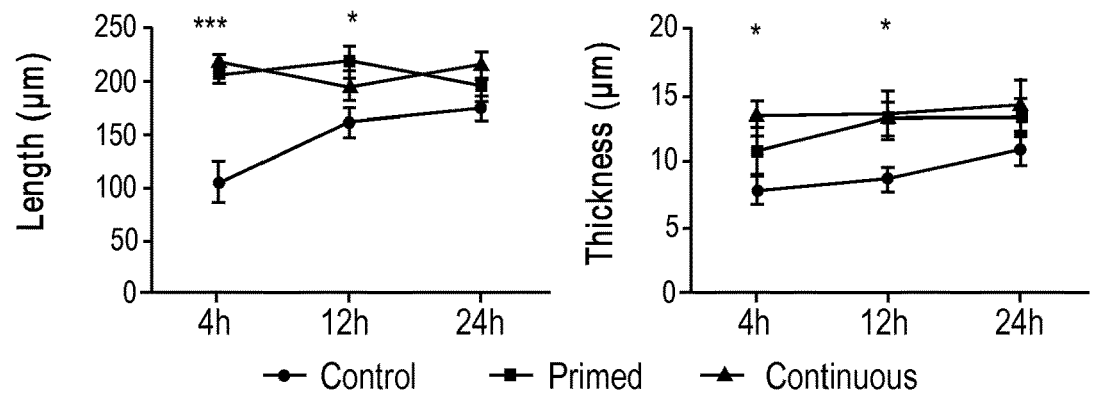

Next the ability for EVCs derived by the three conditions to form cord-like structures on Matrigel was assessed. After 4 hours of culture, some spreading in control EVCs was observed (FIG. 4E). Intriguingly, primed or continuous EVCs were able to reorganize into cord-like structures after just 4 h. Quantification of mean tube length revealed both types of 5% $O_2$ EVCs formed structures with significantly larger mean tube lengths compared to control EVCs after 4 h (FIG. 4F). Over 24 h, the mean tube length of structures formed by continuous or primed EVCs did not change. Contrastingly, the mean tube length of structures formed by control EVCs gradually increased over 24 h, approaching that of primed and continuous EVCs. Examining the mean tube thickness a similar trend was found (FIG. 4F). After 4 hours of culture, primed or continuous EVCs reached their maximum thickness while networks formed by control EVCs increased in mean tube thickness over 24 h.

Figure 4G:
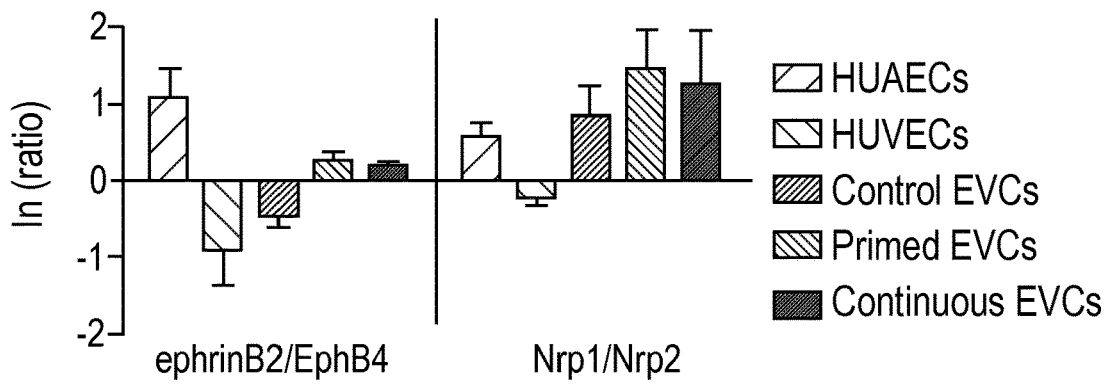

To further define the phenotype of derived ECs, the expression of arterial EC markers, ephrinB2 and Nrp1, and venous markers, EphB4 and Nrp2, compared to control cell types, human umbilical artery ECs (HUAECs) and human umbilical vein ECs (HUVECs) were examined. Expression of these markers was normalized to that by endothelial colony forming cells (ECFCs). The natural log of the ratio of the relative expression of arterial markers ephrinB2 and Nrp1 to the relative expression of venous markers EphB4 and Nrp2 was taken, respectively. This form of analysis yields positive values for arterial cells (e.g. HUAECs) and negative values for venous cells (e.g. HUVECs) (FIG. 4G). When the values were assessed for control, primed, and continuous EVCs, it was found that both primed and continuous EVCs took on a phenotype more similar to that of HUAECs (FIG. 4G). Control EVCs did not demonstrate a clear fate identity toward either lineage. These data suggest that a 5% $O_2$ environment may promote EVCs toward the arterial lineage.

EXAMPLE 7

Role of ROS in 5% O₂ Differentiation

Figure 5A:
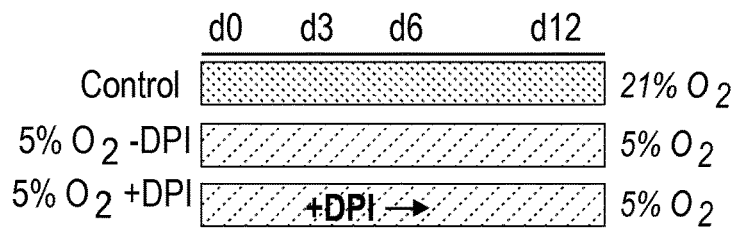
FIG. 5A-D. Role of ROS in EC fate. (A) Schematic of DPI-treated conditions. ROS expression (green) after (B) 3 days in either control (i.e. atmospheric) or 5% $O_2$ conditions and (C) three additional days with or without DPI treatment under 5% $O_2$ conditions. Scale bars are 100 μm. (D) RT-PCR analysis of differentiation products, normalized to control EVCs. *$P<0.05$; $P<0.01$; *$P<0.001$.
Figure 5B:
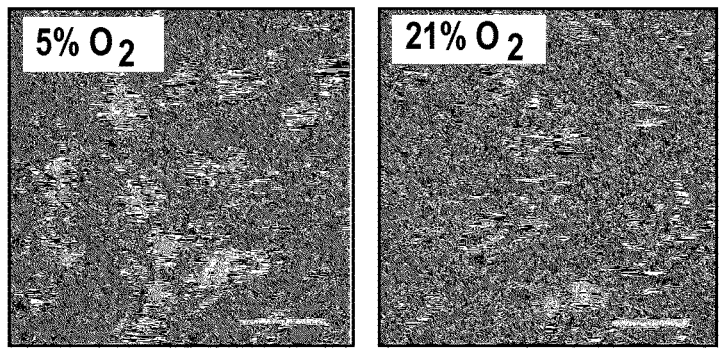
Figure 5C:
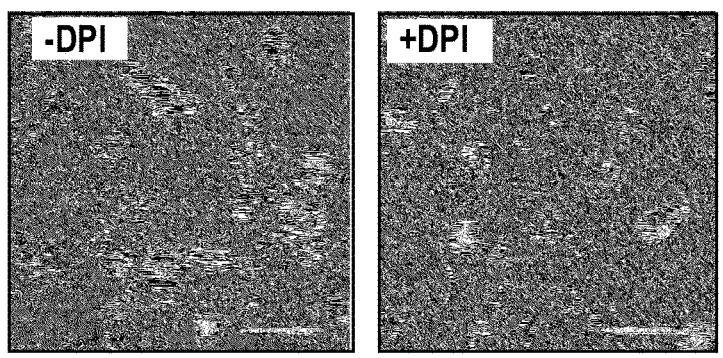

Low oxygen environments promote the generation of reactive oxygen species (ROS), which allow the cells to adapt to lower $O_2$ tensions (Thannickal et al., *American Journal of Physiology—Lung Cellular and Molecular Physiology.* 2000; 279:L1005-L1028). Generation of ROS was analyzed by H2DCF-DA, a redox-sensitive fluorescent dye, during differentiation in 5% $O_2$ and control conditions (FIG. 5A). After just three days, ROS accumulation in the 5% $O_2$ differentiated cells to a greater extent than that in control cells was observed (FIG. 5B). To understand whether there was an association between ROS generation and the distinct phenotypes observed after 12 days, cells were treated the with DPI, a potent inhibitor of ROS. Since it was found that low oxygen conditions during the early stages of differentiation affect endothelial fate, the effect of the addition of DPI to the first half of the differentiation was examined. When DPI was added at day 0, cell attachment and proliferation was severely limited and enough cells for analysis could not be obtain. Alternatively, DPI was added after 3 days of differentiation in order to first allow the cells to attach and grow and then treated them with DPI for a total of 3 days (days 3-6 of differentiation). After three following days of differentiation under DPI-treated conditions (day six total), ROS production was drastically reduced (FIG. 5C).

Figure 5D:
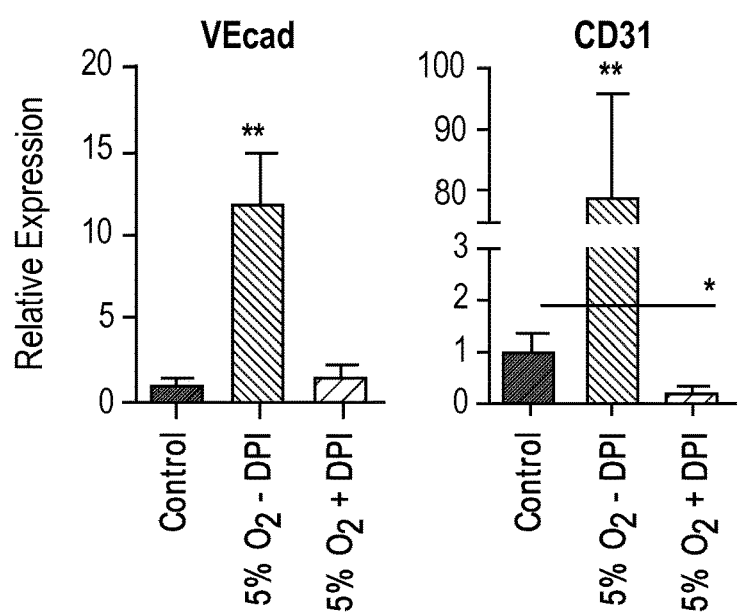

DPI-treated cells were maintained in 5% $O_2$ conditions for the second six days of differentiation but without DPI. After 12 days, DPI-treated cells exhibited similar expression of VEcad but lower expression of CD31 compared to control EVCs (FIG. 5D). Both VEcad and CD31 expression in DPI-treated cells was significantly lower than EVCs differentiated in 5% $O_2$ conditions without DPI (from FIG. 3B). Thus, it is suggested that the presence of DPI abolished differentiating cells' downstream signaling in response to 5% $O_2$ and led to a phenotype more similar to that of atmospheric-derived (i.e. control) cells, implicating ROS in the augmented vascular differentiation capacity under 5% $O_2$ conditions.

Although the invention has been described with reference to the above example, it will be understood that modifications and variations are encompassed within the spirit and scope of the invention. Accordingly, the invention is limited only by the following claims.

What is claimed is:

1. A method of generating early vascular cells (EVCs) comprising endothelial cells (ECs) and pericytes, comprising:
   a) culturing pluripotent stem cells (PSCs) under hypoxic conditions of about 1-5% oxygen on a first two-dimensional culture substrate in a monolayer in a first growth medium for a time suitable to induce differentiation of the PSCs to generate EVCs;
   b) differentiating the cells of a) under hypoxic conditions of about 1-5% oxygen on a second culture substrate in a second growth medium comprising a transforming growth factor-β(TGF-β) inhibitor and a vascular endothelial growth factor (VEGF) for a time suitable to induce differentiation of the cells of b) to generate a population of ECs expressing vascular endothelial cadherin and pericytes expressing platelet-derived growth factor receptor beta and neural/glial antigen 2 (NG2), thereby generating EVCs comprising ECs and pericytes.

2. The method of claim 1, wherein the PSCs are human pluripotent stem cells (hPSCs) that are cultured on a two-dimensional substrate selected from a petri dish, a roller bottle, a flask or a three-dimensional substrate.

3. The method of claim 1, wherein hypoxic conditions are about 5% oxygen.

4. The method of claim 1, wherein the first two-dimensional culture substrate is selected from the group consisting of type I collagen, type IV collagen and fibronectin.

5. The method of claim 1, wherein the ECs are surrounded by the pericytes.

6. The method of claim 1, wherein the TGF-β inhibitor is SB431542.

7. The method of claim 1, wherein the second growth medium comprises from about 1 to 25 μM TGF-β inhibitor.

8. The method of claim 1, wherein the second growth medium comprises 10 μM SB431542.

9. The method of claim 1, wherein the VEGF is VEGF-A.

10. The method of claim 1, wherein the second growth medium comprises from about 10 to 80 ng/ml VEGF.

11. The method of claim 1, wherein the second growth medium comprises 50 ng/ml VEGF.

12. The method of claim 1, wherein the time suitable to induce differentiation in step a) is about 2 to 12 days.

13. The method of claim 1, wherein the time suitable to induce differentiation in step b) is about 2 to 12 days.

14. A method of generating early vascular cells (EVCs) comprising endothelial cells (ECs) and pericytes, comprising:
   a) culturing pluripotent stem cells (PSCs) under hypoxic conditions of about 1-5% oxygen on a first two-dimensional culture substrate in a monolayer in a first growth medium suitable to induce differentiation of the PSCs to generate EVCs;
   b) differentiating the cells of a) under hypoxic conditions of about 1-5% oxygen on a second culture substrate in a second growth medium consisting essentially of a transforming growth factor-β(TGF-β) inhibitor and vascular endothelial growth factor (VEGF), thereby inducing differentiation of the cells of a) into a population of ECs expressing vascular endothelial cadherin and pericytes expressing platelet-derived growth factor receptor beta and neural/glial antigen 2 (NG2), thereby generating EVCs comprising ECs and pericytes.

\* \* \* \* \*